United States Patent
Locke et al.

(10) Patent No.: US 11,471,584 B2
(45) Date of Patent: Oct. 18, 2022

(54) COMPOSITE DRESSINGS FOR IMPROVED GRANULATION AND REDUCED MACERATION WITH NEGATIVE-PRESSURE TREATMENT

(71) Applicant: KCI Licensing, Inc., San Antonio, TX (US)

(72) Inventors: Christopher Brian Locke, Bournemouth (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 130 days.

(21) Appl. No.: 15/997,809

(22) Filed: Jun. 5, 2018

(65) Prior Publication Data
US 2018/0353662 A1 Dec. 13, 2018

Related U.S. Application Data

(60) Provisional application No. 62/633,438, filed on Feb. 21, 2018, provisional application No. 62/625,704, (Continued)

(51) Int. Cl.
*A61M 1/00* (2006.01)
*A61F 13/00* (2006.01)
*A61F 13/02* (2006.01)

(52) U.S. Cl.
CPC .......... *A61M 1/90* (2021.05); *A61F 13/00063* (2013.01); *A61F 13/00068* (2013.01);
(Continued)

(58) Field of Classification Search
CPC ............ A61F 13/00068; A61F 13/0223; A61F 13/0213; A61F 13/0206; A61F 13/0216;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

3M™ Medical Tape 9830, Single Sided Transparent Polyethylene, 63# Liner, Configurable. Retrieved on May 21, 2019. Retrieved from the Internet: <www.3m.com/3M/en_US/company-us/all-3m-products/~/3M-9830-Transparent-Polyethylene-Single-Sided-Medical-Tape-63-Liner/?N=5002385+8729793+3294739632&rt=rud; accessed May 21, 2019>.

(Continued)

*Primary Examiner* — Nicholas J. Weiss
*Assistant Examiner* — Alessandro R Del Priore

(57) ABSTRACT

Dressings for treating a tissue site with negative pressure are disclosed, which may include a dressing having at least three layers assembled in a stacked relationship. In one example embodiment, a first film may comprise a non-porous material and a plurality of fluid restrictions. A first manifold layer may be adjacent to the first film and may comprise a second film of a transparent material having blisters and a manifold area. The first manifold layer may further comprise apertures configured to allow fluid transfer through the second film. A second manifold layer may be adjacent to the first manifold layer and may comprise foam having a contact area that is less than the manifold area of the first manifold layer.

28 Claims, 9 Drawing Sheets

Related U.S. Application Data filed on Feb. 2, 2018, provisional application No. 62/623,325, filed on Jan. 29, 2018, provisional application No. 62/616,244, filed on Jan. 11, 2018, provisional application No. 62/615,821, filed on Jan. 10, 2018, provisional application No. 62/613,494, filed on Jan. 4, 2018, provisional application No. 62/592,950, filed on Nov. 30, 2017, provisional application No. 62/576,498, filed on Oct. 24, 2017, provisional application No. 62/565,754, filed on Sep. 29, 2017, provisional application No. 62/516,540, filed on Jun. 7, 2017, provisional application No. 62/516,550, filed on Jun. 7, 2017, provisional application No. 62/516,566, filed on Jun. 7, 2017.

(52) U.S. Cl.
CPC ...... *A61F 13/0206* (2013.01); *A61F 13/0216* (2013.01); *A61M 1/85* (2021.05); *A61F 2013/00319* (2013.01); *A61F 2013/00357* (2013.01); *A61M 2205/3344* (2013.01); *A61M 2205/50* (2013.01); *A61M 2210/1021* (2013.01)

(58) Field of Classification Search
CPC ........ A61F 2013/00536; A61F 13/0203; A61F 13/0226; A61F 2013/00863; A61F 13/00029; A61F 13/022; A61F 2013/00604; A61F 13/00021; A61F 13/025; A61F 13/512; A61F 2013/00255; A61F 2013/00638; A61F 2013/53081; A61F 13/00063; A61F 2013/00357; A61F 2013/00319; A61M 1/0088; A61M 27/00; A61M 1/0058; A61M 1/0001; A61M 3/0283; A61M 1/0084; A61M 2205/50; A61M 2205/3344; A61M 2210/1021; A61B 46/00

See application file for complete search history.

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,654,060 A | 4/1972 | Goldman | |
| 3,682,180 A | 8/1972 | McFarlane | |
| 3,826,254 A | 7/1974 | Mellor | |
| 3,930,096 A | 12/1975 | Gilpatrick | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,173,046 A | 11/1979 | Gallagher | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,541,426 A | 9/1985 | Webster | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,983,173 A | 1/1991 | Patience et al. | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,308,313 A | 5/1994 | Karami et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,449,352 A * | 9/1995 | Nishino | A61F 13/15731 604/358 |
| 5,466,231 A | 11/1995 | Cercone et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,635,201 A | 6/1997 | Fabo | |
| 5,636,643 A | 6/1997 | Argenta et al. | |
| 5,645,081 A | 7/1997 | Argenta et al. | |
| 5,720,714 A | 2/1998 | Penrose | |
| 5,842,503 A | 12/1998 | Foley | |
| 5,951,505 A | 9/1999 | Gilman et al. | |
| 5,981,822 A | 11/1999 | Addison | |
| 6,019,511 A | 2/2000 | Thomas et al. | |
| 6,071,267 A | 6/2000 | Zamierowski | |
| 6,135,116 A | 10/2000 | Vogel et al. | |
| 6,241,747 B1 | 6/2001 | Ruff | |
| 6,278,036 B1 | 8/2001 | Anhauser et al. | |
| 6,287,316 B1 | 9/2001 | Agarwal et al. | |

(56) References Cited

U.S. PATENT DOCUMENTS

| | | |
|---|---|---|
| 6,345,623 B1 | 2/2002 | Heaton et al. |
| 6,468,626 B1* | 10/2002 | Takai .................... A61F 13/512 |
| | | 428/137 |
| 6,488,643 B1 | 12/2002 | Tumey et al. |
| 6,493,568 B1 | 12/2002 | Bell et al. |
| 6,553,998 B2 | 4/2003 | Heaton et al. |
| 6,623,681 B1 | 9/2003 | Taguchi et al. |
| 6,653,523 B1 | 11/2003 | McCormack et al. |
| 6,685,681 B2 | 2/2004 | Lockwood et al. |
| 6,752,794 B2 | 6/2004 | Lockwood et al. |
| 6,814,079 B2 | 11/2004 | Heaton et al. |
| 6,855,135 B2 | 2/2005 | Lockwood et al. |
| 7,195,624 B2 | 3/2007 | Lockwood et al. |
| 7,338,482 B2 | 3/2008 | Lockwood et al. |
| 7,381,859 B2 | 6/2008 | Hunt et al. |
| 7,534,927 B2 | 5/2009 | Lockwood et al. |
| 7,846,141 B2 | 12/2010 | Weston |
| 7,867,206 B2 | 1/2011 | Lockwood et al. |
| 7,880,050 B2 | 2/2011 | Robinson et al. |
| 7,896,864 B2 | 3/2011 | Lockwood et al. |
| 7,951,100 B2 | 5/2011 | Hunt et al. |
| 7,988,680 B2 | 8/2011 | Lockwood et al. |
| 8,062,273 B2 | 11/2011 | Weston |
| 8,148,595 B2 | 4/2012 | Robinson et al. |
| 8,168,848 B2 | 5/2012 | Lockwood et al. |
| 8,187,210 B2 | 5/2012 | Hunt et al. |
| 8,216,198 B2 | 7/2012 | Heagle et al. |
| 8,246,592 B2 | 8/2012 | Lockwood et al. |
| 8,251,979 B2 | 8/2012 | Malhi |
| 8,257,327 B2 | 9/2012 | Blott et al. |
| 8,350,116 B2 | 1/2013 | Lockwood et al. |
| 8,398,614 B2 | 3/2013 | Blott et al. |
| 8,449,509 B2 | 5/2013 | Weston |
| 8,454,580 B2 | 6/2013 | Locke et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 | 3/2014 | Hunt et al. |
| 8,679,081 B2 | 3/2014 | Heagle et al. |
| 8,680,359 B2 | 3/2014 | Robinson et al. |
| 8,690,844 B2 | 4/2014 | Locke et al. |
| 8,834,451 B2 | 9/2014 | Blott et al. |
| 8,884,094 B2 | 11/2014 | Lockwood et al. |
| 8,926,592 B2 | 1/2015 | Blott et al. |
| 9,017,302 B2 | 4/2015 | Vitaris et al. |
| 9,168,179 B2 | 10/2015 | Robinson et al. |
| 9,198,801 B2 | 12/2015 | Weston |
| 9,198,802 B2 | 12/2015 | Robinson et al. |
| 9,211,365 B2 | 12/2015 | Weston |
| 9,289,542 B2 | 3/2016 | Blott et al. |
| 9,352,075 B2 | 5/2016 | Robinson et al. |
| 9,445,947 B2 | 9/2016 | Hunt et al. |
| 9,526,660 B2 | 12/2016 | Robinson et al. |
| 9,844,471 B2 | 12/2017 | Lockwood et al. |
| 10,016,544 B2 | 7/2018 | Coulthard et al. |
| 10,045,886 B2 | 8/2018 | Lockwood et al. |
| 2001/0043943 A1 | 11/2001 | Coffey |
| 2002/0077661 A1 | 6/2002 | Saadat |
| 2002/0082567 A1 | 6/2002 | Lockwood et al. |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0203011 A1 | 10/2003 | Abuelyaman et al. |
| 2004/0030304 A1 | 2/2004 | Hunt et al. |
| 2004/0126413 A1 | 7/2004 | Sigurjonsson et al. |
| 2004/0138604 A1 | 7/2004 | Sigurjonsson et al. |
| 2004/0148756 A1 | 8/2004 | Pommer |
| 2004/0261295 A1 | 12/2004 | Meschter |
| 2005/0226917 A1 | 10/2005 | Burton |
| 2006/0241542 A1 | 10/2006 | Gudnason et al. |
| 2007/0038172 A1 | 2/2007 | Zamierowski |
| 2007/0185426 A1 | 8/2007 | Ambrosio et al. |
| 2008/0300555 A1 | 12/2008 | Olson et al. |
| 2009/0047495 A1 | 2/2009 | Hubbs |
| 2009/0082746 A1 | 3/2009 | Thomas et al. |
| 2009/0221979 A1* | 9/2009 | Huang ................ A61F 13/5126 |
| | | 604/367 |
| 2009/0234307 A1 | 9/2009 | Vitaris |
| 2009/0293887 A1 | 12/2009 | Wilkes et al. |
| 2010/0030170 A1 | 2/2010 | Keller et al. |
| 2010/0030178 A1 | 2/2010 | MacMeccan et al. |
| 2010/0036334 A1 | 2/2010 | Heagle et al. |
| 2010/0063484 A1 | 3/2010 | Heagle |
| 2010/0069863 A1 | 3/2010 | Olson |
| 2010/0069885 A1 | 3/2010 | Stevenson et al. |
| 2010/0106115 A1* | 4/2010 | Hardman ............... A61M 27/00 |
| | | 604/319 |
| 2010/0159192 A1 | 6/2010 | Cotton |
| 2010/0291184 A1 | 11/2010 | Clark et al. |
| 2010/0305490 A1 | 12/2010 | Coulthard et al. |
| 2011/0054422 A1 | 3/2011 | Locke et al. |
| 2011/0117178 A1 | 5/2011 | Junginger |
| 2011/0160686 A1 | 6/2011 | Ueda et al. |
| 2011/0178451 A1 | 7/2011 | Robinson et al. |
| 2011/0213287 A1* | 9/2011 | Lattimore ......... A61F 13/00021 |
| | | 602/46 |
| 2011/0224631 A1* | 9/2011 | Simmons .......... A61F 13/00029 |
| | | 604/319 |
| 2011/0282309 A1 | 11/2011 | Adie et al. |
| 2011/0313374 A1 | 12/2011 | Lockwood et al. |
| 2012/0046603 A1 | 2/2012 | Vinton |
| 2012/0157945 A1 | 6/2012 | Robinson et al. |
| 2012/0209226 A1 | 8/2012 | Simmons et al. |
| 2012/0238932 A1* | 9/2012 | Atteia ................. A61F 13/0223 |
| | | 602/52 |
| 2013/0053748 A1 | 2/2013 | Cotton |
| 2013/0152945 A1 | 6/2013 | Locke et al. |
| 2013/0261534 A1 | 10/2013 | Niezgoda et al. |
| 2014/0031771 A1 | 1/2014 | Locke et al. |
| 2014/0052041 A1* | 2/2014 | Barberio .............. A61F 13/0209 |
| | | 602/48 |
| 2014/0058309 A1 | 2/2014 | Addison et al. |
| 2014/0081192 A1 | 3/2014 | Wenske et al. |
| 2014/0094730 A1 | 4/2014 | Greener et al. |
| 2014/0107562 A1 | 4/2014 | Dorian et al. |
| 2014/0163447 A1 | 6/2014 | Wieland et al. |
| 2014/0163491 A1 | 6/2014 | Schuessler et al. |
| 2014/0188059 A1 | 7/2014 | Robinson et al. |
| 2014/0200532 A1 | 7/2014 | Robinson et al. |
| 2014/0228787 A1 | 8/2014 | Croizat et al. |
| 2014/0236112 A1 | 8/2014 | Von Wolff et al. |
| 2014/0350494 A1 | 11/2014 | Hartwell et al. |
| 2014/0364819 A1 | 12/2014 | VanDelden |
| 2015/0038933 A1* | 2/2015 | Day ................... A61F 13/51113 |
| | | 428/131 |
| 2015/0057624 A1 | 2/2015 | Simmons et al. |
| 2015/0080788 A1 | 3/2015 | Blott et al. |
| 2015/0119830 A1 | 4/2015 | Luckemeyer et al. |
| 2015/0119831 A1 | 4/2015 | Robinson et al. |
| 2015/0119833 A1* | 4/2015 | Coulthard ................ A61M 1/80 |
| | | 604/319 |
| 2015/0141941 A1 | 5/2015 | Allen et al. |
| 2015/0150729 A1 | 6/2015 | Dagger et al. |
| 2015/0174291 A1 | 6/2015 | Zimnitsky et al. |
| 2015/0174304 A1 | 6/2015 | Askem et al. |
| 2015/0201954 A1* | 7/2015 | Pratt .................... A61B 17/322 |
| | | 606/131 |
| 2015/0290042 A1 | 10/2015 | Freer et al. |
| 2015/0290050 A1* | 10/2015 | Wada ...................... B32B 37/10 |
| | | 156/196 |
| 2015/0320434 A1 | 11/2015 | Ingram et al. |
| 2015/0320602 A1* | 11/2015 | Locke ............... A61F 13/00017 |
| | | 606/213 |
| 2015/0320603 A1 | 11/2015 | Locke et al. |
| 2016/0000610 A1 | 1/2016 | Riesinger |
| 2016/0015571 A1 | 1/2016 | Robinson et al. |
| 2016/0022885 A1 | 1/2016 | Dunn et al. |
| 2016/0030646 A1 | 2/2016 | Hartwell et al. |
| 2016/0095754 A1 | 4/2016 | Andrews et al. |
| 2016/0144084 A1 | 5/2016 | Collinson et al. |
| 2016/0144085 A1* | 5/2016 | Melin .................... A61M 1/90 |
| | | 604/319 |

(56) References Cited

U.S. PATENT DOCUMENTS

| | | |
|---|---|---|
| 2016/0166744 A1 | 6/2016 | Hartwell |
| 2016/0175156 A1 | 6/2016 | Locke et al. |
| 2016/0199546 A1 | 7/2016 | Chao |
| 2016/0199550 A1 | 7/2016 | Seddon et al. |
| 2016/0220742 A1 | 8/2016 | Robinson et al. |
| 2016/0262672 A1 | 9/2016 | Hammond et al. |
| 2016/0354253 A1 | 12/2016 | Hunt et al. |
| 2017/0014273 A1 | 1/2017 | Woodroof |
| 2017/0079846 A1 | 3/2017 | Locke et al. |
| 2017/0095374 A1 | 4/2017 | Lauer |
| 2017/0143552 A1* | 5/2017 | Hartwell ............ A61F 13/0233 |
| 2017/0172807 A1 | 6/2017 | Robinson et al. |
| 2017/0174852 A1 | 6/2017 | Hanschen et al. |
| 2017/0209312 A1 | 7/2017 | Kanchagar et al. |
| 2017/0258640 A1 | 9/2017 | Ahsani Ghahreman et al. |
| 2017/0312406 A1 | 11/2017 | Svensby |
| 2017/0348154 A1 | 12/2017 | Robinson et al. |
| 2017/0348158 A1 | 12/2017 | You et al. |
| 2018/0071148 A1 | 3/2018 | Lockwood et al. |
| 2018/0289872 A1 | 10/2018 | Coulthard et al. |
| 2018/0296394 A1 | 10/2018 | Barberio |
| 2019/0117472 A1* | 4/2019 | Erdem ..................... B32B 7/09 |
| 2019/0184075 A1* | 6/2019 | Roos ................ A61F 13/00068 |

FOREIGN PATENT DOCUMENTS

| | | | | |
|---|---|---|---|---|
| AU | 755496 B2 | 12/2002 | | |
| CA | 2005436 A1 | 6/1990 | | |
| CN | 106390213 A | 2/2017 | | |
| DE | 26 40 413 A1 | 3/1978 | | |
| DE | 43 06 478 A1 | 9/1994 | | |
| DE | 29 504 378 U1 | 9/1995 | | |
| EP | 0100148 A1 | 2/1984 | | |
| EP | 0117632 A2 | 9/1984 | | |
| EP | 0161865 A2 | 11/1985 | | |
| EP | 0174803 A2 * | 3/1986 | ............ | A61L 15/26 |
| EP | 0358302 A2 | 3/1990 | | |
| EP | 1018967 A1 | 7/2000 | | |
| GB | 692578 A | 6/1953 | | |
| GB | 2 195 255 A | 4/1988 | | |
| GB | 2 197 789 A | 6/1988 | | |
| GB | 2 220 357 A | 1/1990 | | |
| GB | 2 235 877 A | 3/1991 | | |
| GB | 2 329 127 A | 3/1999 | | |
| GB | 2 333 965 A | 8/1999 | | |
| GB | 2468905 A | 9/2010 | | |
| JP | 2008073187 A | 4/2008 | | |
| JP | 4129536 B2 | 8/2008 | | |
| SG | 71559 | 4/2002 | | |
| WO | 80/02182 A1 | 10/1980 | | |
| WO | 87/04626 A1 | 8/1987 | | |
| WO | 90/010424 A1 | 9/1990 | | |
| WO | 93/009727 A1 | 5/1993 | | |
| WO | 9319709 A1 | 10/1993 | | |
| WO | 94/020041 A1 | 9/1994 | | |
| WO | 96/05873 A1 | 2/1996 | | |
| WO | 97/18007 A1 | 5/1997 | | |
| WO | 99/13793 A1 | 3/1999 | | |
| WO | 0185248 A1 | 11/2001 | | |
| WO | 2007113597 A2 | 10/2007 | | |
| WO | 2009002260 A1 | 12/2008 | | |
| WO | 2010061228 A1 | 6/2010 | | |
| WO | 2011008497 A2 | 1/2011 | | |
| WO | 2011121127 A1 | 10/2011 | | |
| WO | 2011127188 A2 | 10/2011 | | |
| WO | 2011135286 A1 | 11/2011 | | |
| WO | 2012063725 A1 | 5/2012 | | |
| WO | 2014140608 A1 | 9/2014 | | |
| WO | WO-2015098373 A1 * | 7/2015 | ............ | B32B 5/022 |
| WO | 2015168681 A1 | 11/2015 | | |
| WO | 2015173547 A1 | 11/2015 | | |
| WO | 2015193257 A1 | 12/2015 | | |
| WO | 2016014645 A1 | 1/2016 | | |
| WO | 2016015001 A2 | 1/2016 | | |
| WO | 2017040045 A1 | 3/2017 | | |
| WO | 2017119996 A1 | 7/2017 | | |

OTHER PUBLICATIONS

3M™ Medical Tape 9948, Single Sided Thermoplastic Elastomer Medical Tape, 63# liner, Configurable. Retrieved May 21, 2019. Retrieved from the Internet: <www.3m.com/3M/en_US/company-us/all-3m-products/~/3M-9948-Single-Sided-Thermoplastic-Elastomer-TPE-Medical-Incise-Tape/?N=5002385+4294834151&rt=d; accessed May 21, 2019>.

International Search Report and Written Opinion for related application PCT/US2018/036013, dated Aug. 7, 2018.

International Search Report and Written Opinion for related application PCT/US2018/035945, dated Aug. 24, 2018.

International Search Report and Written Opinion for related application PCT/US2018/036074, dated Aug. 24, 2018.

International Search Report and Written Opinion for related application PCT/US2018/035957, dated Sep. 28, 2018.

International Search Report and Written Opinion for related application PCT/US2018/035995, dated Oct. 1, 2018.

International Search Report and Written Opinion for related application PCT/US2018/036021, dated Aug. 24, 2018.

International Search Report and Written Opinion for related application PCT/US2018/036019, dated Oct. 18, 2018.

International Search Report and Written Opinion for related application PCT/US2018/036054, dated Aug. 24, 2018.

International Search Report and Written Opinion for related application PCT/US2018/036049, dated Aug. 29, 2018.

International Search Report and Written Opinion for related application PCT/US2018/036077, dated Aug. 24, 2018.

International Search Report and Written Opinion for related application PCT/US2018/036129, dated Oct. 8, 2018.

Heit, et al., "Foam Pore Size Is a Critical Interface Parameter of Suction-Based Wound Healing Devices," copyright 2012 by the American Society of Plastic Surgeons (www. PRSJournal.com) (Year: 2011).

Office Action for related U.S. Appl. No. 16/000,284, dated Sep. 23, 2019.

Office Action for related U.S. Appl. No. 16/000,284, dated Jun. 8, 2020.

Office Action for related U.S. Appl. No. 15/997,833, dated Jun. 19, 2020.

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

(56) References Cited

OTHER PUBLICATIONS

PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture" Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Septembers, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž.Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96,167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Law, Definitions for Hydrophilicity, Hydrophobicity, and Superhydrophobicity: Getting the Basics Right, The Journal of Physical Chemistry Letters, Feb. 20, 2014, 686-688.
Office Action for related U.S. Appl. No. 15/997,841, dated Aug. 5, 2020.
Office Action for related U.S. Appl. No. 15/997,818, dated Sep. 3, 2020.
Office Action for related U.S. Appl. No. 15/997,761, dated Sep. 14, 2020.
Office Action for related U.S. Appl. No. 15/997,923, dated Sep. 17, 2020.
Office Action for related U.S. Appl. No. 16/000,737, dated Sep. 29, 2020.
Office Action for related U.S. Appl. No. 16/000,002, dated Oct. 28, 2020.
Singaporean Office Action for related application 11201909383P, dated Oct. 5, 2020.
Singaporean Office Action for related application 11201909371P, dated Oct. 13, 2020.
Definition of "bonded," Merriam-Webster, www.https://www.merriam-webster.com/dictionary/bonded, retrieved Dec. 11, 2020.
Burkitt et al., "New Technologies in Silicone Adhesives: Silicone-based film adhesives, PSAs and tacky gels each offer unique advantages"; ASI (Adhesives & Sealants Industry), Aug. 1, 2012; https://www.adhesivesmag.com/articles/91217-new-technologies-in-silicone-adhesives.
Office Action for related U.S. Appl. No. 16/000,284, dated Nov. 25, 2020.
Office Action for related U.S. Appl. No. 16/000,411, dated Dec. 7, 2020.
Office Action for related U.S. Appl. No. 16/000,383, dated Jul. 8, 2020.
Bastarrachea et al. Engineering Properties of Polymeric-Based Antimicrobial Films for Food Packaging: A Review. Food Engineering Reviews. 3. 2011. pp. 79-93.
Selke et al. Packaging: Polymers for Containers, Encyclopedia of Materials: Science and Technology, Elsevier, 2001, pp. 6646-6652.
Office Action for related U.S. Appl. No. 16/000,368, dated Dec. 14, 2020.
Office Action for related U.S. Appl. No. 15/997,818, dated Jan. 27, 2021.
Office Action for related U.S. Appl. No. 15/997,841, dated Jan. 27, 2021.
Office Action for related U.S. Appl. No. 15/997,833, dated Mar. 26, 2021.

(56) References Cited

OTHER PUBLICATIONS

Office Action for related U.S. Appl. No. 16/000,215, dated Apr. 12, 2021.
Chinese Office Action for related application 2018800367248, dated Apr. 28, 2021.
Office Action for related U.S. Appl. No. 15/997,833, dated Jun. 7, 2021.
Office Action for related U.S. Appl. No. 15/997,841, dated Jun. 8, 2021.
Chinese Office Action for related application 201880048393X, dated May 26, 2021.
Chinese Office Action for related application 2018800436430, dated Jun. 8, 2021.
Office Action for related U.S. Appl. No. 15/997,923, dated Jul. 23, 2021.
Office Action for related U.S. Appl. No. 15/997,818, dated Aug. 10, 2021.
Office Action for related U.S. Appl. No. 16/684,060, dated Aug. 27, 2021.
Office Action for related U.S. Appl. No. 16/000,411, dated Aug. 27, 2021.
Office action for related U.S. Appl. No. 15/997,833, dated Sep. 7, 2021.
Office action for related U.S. Appl. No. 16/000,002, dated Oct. 4, 2021.
Office Action for related U.S. Appl. No. 15/997,923, dated Nov. 16, 2021.
Office Action for related U.S. Appl. No. 16/000,411, dated Jan. 31, 2022.
Office Action for related U.S. Appl. No. 16/959,651, dated Feb. 15, 2022.
Japanese Office Action for related application 2019-566886, dated Mar. 29, 2022.
Office Action for related U.S. Appl. No. 16/000,383, dated Mar. 31, 2022.
Pappas et al, "Wettability Tests of Polymer Films and Fabrics and Determination of Their Surface Energy by Contact-Angle Methods," Army Research Laboratory, ARL-TR-4056, Mar. 2007, p. 5.
Baltex, Technical Fabrics & Technical Textile Products, https://www.baltex.co.uk/products/xd-spacer-fabrics/, accessed Apr. 20, 2022.
Yimin Qin, Applications of Advanced Technologies in the Development of Functional Medical Textile Materials, Medical Textile Materials, 2016, pp. 55-70, Woodhead Publishing.
Baltex, Technical Fabrics & Technical Textile Products http://web.archive.org/web/20150118084138/http://www.baltex.co.uk/products/Healthcarefabrics/, 2015.
Office Action for related U.S. Appl. No. 17/204,548, dated Apr. 19, 2022.
Office Action for related application U.S. Appl. No. 15/997,818, dated Jun. 9, 2022.
Japanese Office Action for related application 2019-567267, dated Jun. 7, 2022.
Japanese Office Action for related application 2019-566969, dated Jul. 7, 2022.
Japanese Office Action for related application 2019-567266, dated Jun. 7, 2022.
Japanese Office Action for related application 2019-566908, dated Aug. 2, 2022.

\* cited by examiner

COMPOSITE DRESSINGS FOR IMPROVED GRANULATION AND REDUCED MACERATION WITH NEGATIVE-PRESSURE TREATMENT

RELATED APPLICATION

This application claims the benefit, under 35 U.S.C. § 119(e), of the filing of U.S. Provisional Patent Application Ser. No. 62/633,438, entitled "COMPOSITE DRESSINGS FOR IMPROVED GRANULATION AND REDUCED MACERATION WITH NEGATIVE-PRESSURE TREATMENT," filed Feb. 21, 2018; U.S. Provisional Patent Application Ser. No. 62/623,325, entitled "METHODS FOR MANUFACTURING AND ASSEMBLING DUAL MATERIAL TISSUE INTERFACE FOR NEGATIVE-PRESSURE THERAPY," filed Jan. 29, 2018; U.S. Provisional Patent Application Ser. No. 62/625,704, entitled "CUSTOMIZABLE COMPOSITE DRESSINGS FOR IMPROVED GRANULATION AND REDUCED MACERATION WITH NEGATIVE-PRESSURE TREATMENT," filed Feb. 2, 2018; U.S. Provisional Patent Application Ser. No. 62/616,244, entitled "COMPOSITE DRESSINGS FOR IMPROVED GRANULATION AND REDUCED MACERATION WITH NEGATIVE-PRESSURE TREATMENT," filed Jan. 11, 2018; U.S. Provisional Patent Application Ser. No. 62/615,821, entitled "METHODS FOR MANUFACTURING AND ASSEMBLING DUAL MATERIAL TISSUE INTERFACE FOR NEGATIVE-PRESSURE THERAPY," filed Jan. 10, 2018; U.S. Provisional Patent Application Ser. No. 62/613,494, entitled "PEEL AND PLACE DRESSING FOR THICK EXUDATE AND INSTILLATION," filed Jan. 4, 2018; U.S. Provisional Patent Application Ser. No. 62/592,950, entitled "MULTI-LAYER WOUND FILLER FOR EXTENDED WEAR TIME," filed Nov. 30, 2017; U.S. Provisional Patent Application Ser. No. 62/576,498, entitled "SYSTEMS, APPARATUSES, AND METHODS FOR NEGATIVE-PRESSURE TREATMENT WITH REDUCED TISSUE IN-GROWTH," filed Oct. 24, 2017; U.S. Provisional Patent Application Ser. No. 62/565,754, entitled "COMPOSITE DRESSINGS FOR IMPROVED GRANULATION AND REDUCED MACERATION WITH NEGATIVE-PRESSURE TREATMENT," filed Sep. 29, 2017; U.S. Provisional Patent Application Ser. No. 62/516,540, entitled "TISSUE CONTACT INTERFACE," filed Jun. 7, 2017; U.S. Provisional Patent Application Ser. No. 62/516,550, entitled "COMPOSITE DRESSINGS FOR IMPROVED GRANULATION AND REDUCED MACERATION WITH NEGATIVE-PRESSURE TREATMENT" filed Jun. 7, 2017; and U.S. Provisional Patent Application Ser. No. 62/516,566, entitled "COMPOSITE DRESSINGS FOR IMPROVED GRANULATION AND REDUCED MACERATION WITH NEGATIVE-PRESSURE TREATMENT" filed Jun. 7, 2017, each of which is incorporated herein by reference for all purposes.

TECHNICAL FIELD

The invention set forth in the appended claims relates generally to tissue treatment systems and more particularly, but without limitation, to dressings for tissue treatment with negative pressure and methods of using the dressings for tissue treatment with negative pressure.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," "vacuum-assisted closure," and "topical negative-pressure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

There is also widespread acceptance that cleansing a tissue site can be highly beneficial for new tissue growth. For example, a wound can be washed out with a stream of liquid solution, or a cavity can be washed out using a liquid solution for therapeutic purposes. These practices are commonly referred to as "irrigation" and "lavage" respectively. "Instillation" is another practice that generally refers to a process of slowly introducing fluid to a tissue site and leaving the fluid for a prescribed period of time before removing the fluid. For example, instillation of topical treatment solutions over a wound bed can be combined with negative-pressure therapy to further promote wound healing by loosening soluble contaminants in a wound bed and removing infectious material. As a result, soluble bacterial burden can be decreased, contaminants removed, and the wound cleansed.

While the clinical benefits of negative-pressure therapy and/or instillation therapy are widely known, improvements to therapy systems, components, and processes may benefit healthcare providers and patients.

BRIEF SUMMARY

New and useful systems, apparatuses, and methods for treating tissue in a negative-pressure therapy environment are set forth in the appended claims. Illustrative embodiments are also provided to enable a person skilled in the art to make and use the claimed subject matter.

For example, in some embodiments, a dressing for treating a tissue site with negative pressure may comprise a first film having a non-porous material, a first manifold layer adjacent to the first film and having a second film of transparent material, and a second manifold layer adjacent to the first manifold layer. The first film may further include a plurality of fluid restrictions. The second film of transparent material of the first manifold layer may include blisters and a manifold area, as well as apertures configured to allow fluid transfer through the second film. The second manifold layer may include a foam having a contact area that is less than the manifold area.

In additional embodiments, a dressing for treating a tissue site with negative pressure may comprise a film layer of non-porous material, a plurality of fluid restrictions through the film layer, a first manifold layer adjacent to the film layer, and a second manifold layer adjacent to the first manifold layer. The first manifold layer may include a transparent material and apertures configured to allow fluid transfer through the first manifold layer. The second manifold layer may include a foam. The transparent material of the first manifold layer may be exposed around the foam.

In further embodiments, a dressing for treating a tissue site with negative pressure may comprise a fluid control layer, a first manifold layer adjacent to the fluid control layer, and a second manifold layer adjacent to the first manifold layer. The first manifold layer may be configured to allow visibility of at least part of the tissue site through the first manifold layer. The first manifold may be visible around the second manifold layer.

In yet additional embodiments, a dressing for treating a tissue site with negative pressure may comprise a lower layer comprising a first film of at least partially transparent, liquid-impermeable material, an upper layer positioned above the lower layer, and an intermediate layer between the lower layer and the upper layer. The first film may further include a plurality of fluid restrictions to allow the passage of fluid from a wound site through the lower layer. The second film may include a second transparent material and a fluid port for mating with a source of negative pressure. The intermediate layer may comprise foam, wherein the area of the foam is less than the area of the lower layer to allow visualization of a wound site underneath the upper and lower layers. In some embodiments, the area of the foam may be less than 50% of the area of the lower layer. In additional embodiments, the dressing may further include a third film coupled to the lower layer opposite the upper layer. The third film may include a hydrophobic material having a plurality of apertures. In some embodiments, the hydrophobic material may be a silicone material.

In still additional embodiments, a dressing for treating a tissue site with negative pressure may comprise a first film comprising a non-porous material, a second film adjacent to the first film, and a manifold layer adjacent to the second film. The second film may include a transparent material and apertures configured to allow fluid transfer through the transparent material. The manifold layer may include foam having a contact area that is less than the area of the second film.

In yet additional embodiments, a dressing for treating a tissue site with negative pressure may comprise a first film comprising a non-porous material and a plurality of fluid restrictions, a second film adjacent to the first film, and a manifold layer adjacent to the second film. The second film may include a transparent material having blisters. The second film may also include apertures configured to allow fluid transfer through the transparent material. The manifold layer may include foam having a contact area that is less than the area of the second film.

In still additional embodiments, a dressing for treating a tissue site with negative pressure may comprise a first layer comprising a first non-porous material, a second layer adjacent to the first layer, and a third layer adjacent to the second layer. The second layer may include a transparent material having apertures configured to allow fluid transfer through the second layer. The third layer may include a foam having a contact area that is less than an area of the transparent material of the second layer.

In yet further embodiments, a method for treating a tissue site may comprise positioning a dressing on the tissue site, inspecting the position of the dressing against areas of the tissue site, and adjusting the position of the dressing. The dressing may comprise a first film comprising a non-porous material and having a plurality of fluid restrictions, a first manifold layer adjacent to the first film, and a second manifold layer adjacent to the first manifold layer. The first manifold layer may include a second film of a transparent material having a manifold area comprising blisters and apertures. The second manifold layer may include a foam having a contact area that is less than the manifold area. The step of inspecting the position of the dressing against areas of the tissue site may include visualizing the areas of the tissue site through portions of the first film and first manifold layer. Adjusting the position of the dressing may be performed so that the manifold area of the dressing substantially corresponds to areas of the tissue site within borders of the tissue site.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
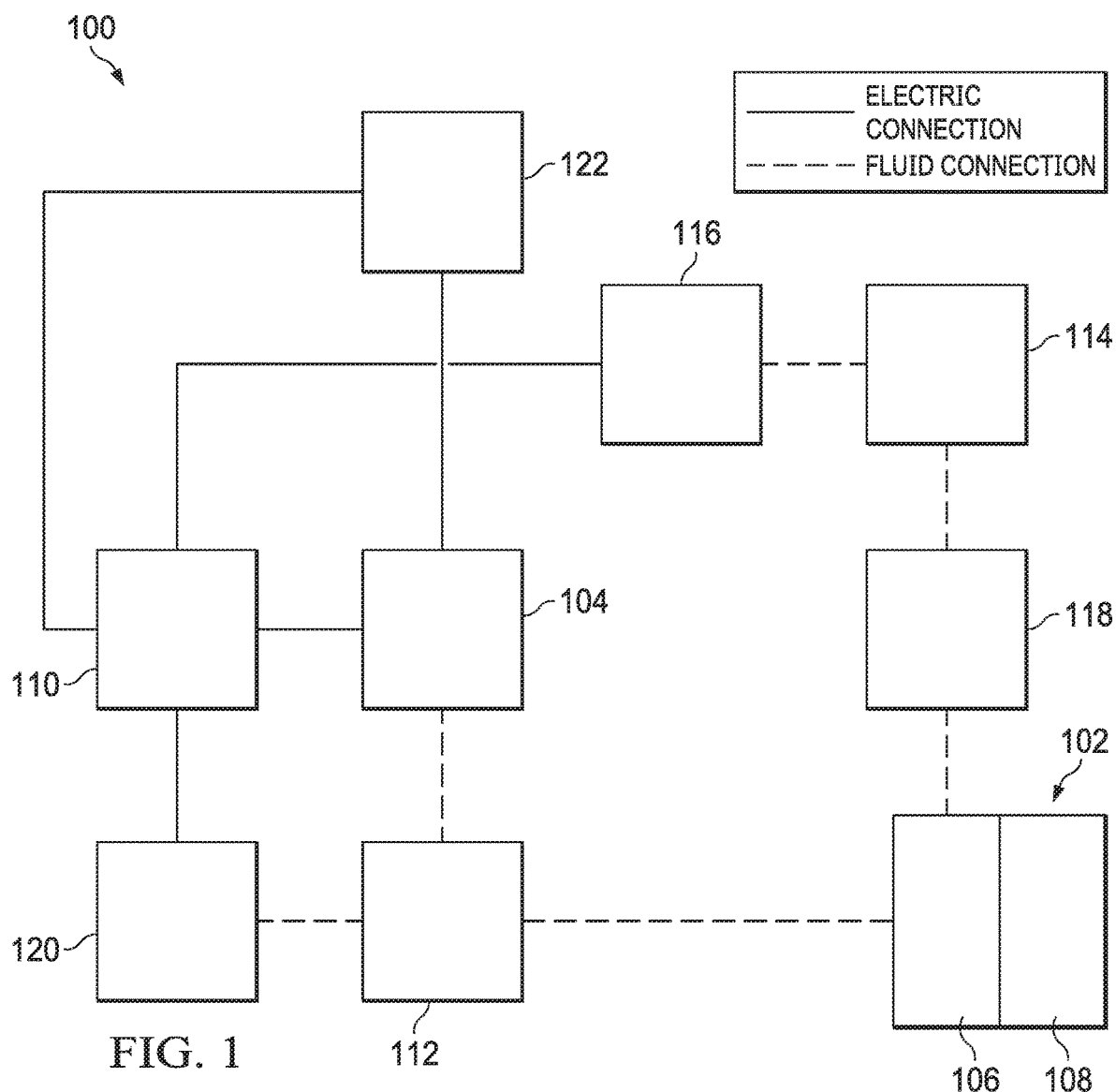
FIG. 1 is a functional block diagram of an example embodiment of a therapy system that can provide tissue treatment in accordance with this specification.

FIG. 1 is a simplified functional block diagram of an example embodiment of a therapy system 100 that can provide negative-pressure therapy with instillation of topical treatment solutions in accordance with this specification.

The term "tissue site" in this context broadly refers to a wound, defect, or other treatment target located on or within tissue, including but not limited to, a surface wound, bone tissue, adipose tissue, muscle tissue, neural tissue, dermal tissue, vascular tissue, connective tissue, cartilage, tendons, or ligaments. The term "tissue site" may also refer to areas of any tissue that are not necessarily wounded or defective, but are instead areas in which it may be desirable to add or promote the growth of additional tissue. For example, negative pressure may be applied to a tissue site to grow additional tissue that may be harvested and transplanted. A surface wound, as used herein, is a wound on the surface of a body that is exposed to the outer surface of the body, such as injury or damage to the epidermis, dermis, and/or subcutaneous layers. Surface wounds may include ulcers or closed incisions, for example. A surface wound, as used herein, does not include wounds within an intra-abdominal cavity. A wound may include chronic, acute, traumatic, subacute, and dehisced wounds, partial-thickness burns, ulcers (such as diabetic, pressure, or venous insufficiency ulcers), flaps, and grafts, for example.

The therapy system 100 may include negative-pressure supply, and may include or be configured to be coupled to a distribution component, such as a dressing. In general, a distribution component may refer to any complementary or ancillary component configured to be fluidly coupled to a negative-pressure supply in a fluid path between a negative-pressure supply and a tissue site. A distribution component is preferably detachable, and may be disposable, reusable, or recyclable. For example, a dressing 102 may be fluidly coupled to a negative-pressure source 104, as illustrated in FIG. 1. A dressing may include a cover, a tissue interface, or both in some embodiments. The dressing 102, for example, may include a cover 106 and a tissue interface 108. A regulator or a controller, such as a controller 110, may also be coupled to the negative-pressure source 104.

In some embodiments, a dressing interface may facilitate coupling the negative-pressure source 104 to the dressing 102. For example, such a dressing interface may be a SENSAT.R.A.C.™ Pad available from Kinetic Concepts, Inc. of San Antonio, Tex. The therapy system 100 may optionally include a fluid container, such as a container 112, coupled to the dressing 102 and to the negative-pressure source 104.

The therapy system 100 may also include a source of instillation solution. For example, a solution source 114 may be fluidly coupled to the dressing 102, as illustrated in the example embodiment of FIG. 1. The solution source 114 may be fluidly coupled to a positive-pressure source, such as the positive-pressure source 116, in some embodiments, or may be fluidly coupled to the negative-pressure source 104. A regulator, such as an instillation regulator 118, may also be fluidly coupled to the solution source 114 and the dressing 102. In some embodiments, the instillation regulator 118 may also be fluidly coupled to the negative-pressure source 104 through the dressing 102, as illustrated in the example of FIG. 1.

Additionally, the therapy system 100 may include sensors to measure operating parameters and provide feedback signals to the controller 110 indicative of the operating parameters. As illustrated in FIG. 1, for example, the therapy system 100 may include a first sensor 120 and a second sensor 122 coupled to the controller 110. The first sensor 120 may also be coupled or configured to be coupled to a distribution component and to the negative-pressure source 104.

Components may be fluidly coupled to each other to provide a path for transferring fluids (i.e., liquid and/or gas) between the components. For example, components may be fluidly coupled through a fluid conductor, such as a tube. A "tube," as used herein, broadly includes a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may also be coupled by virtue of physical proximity, being integral to a single structure, or being formed from the same piece of material. Moreover, some fluid conductors may be molded into or otherwise integrally combined with other components. Coupling may also include mechanical, thermal, electrical, or chemical coupling (such as a chemical bond) in some contexts. For example, a tube may mechanically and fluidly couple the dressing 102 to the container 112 in some embodiments.

In general, components of the therapy system 100 may be coupled directly or indirectly. For example, the negative-pressure source 104 may be directly coupled to the controller 110, and may be indirectly coupled to the dressing 102 through the container 112.

A negative-pressure supply, such as the negative-pressure source 104, may be a reservoir of air at a negative pressure, or may be a manual or electrically-powered device that can reduce the pressure in a sealed volume, such as a vacuum pump, a suction pump, a wall suction port available at many healthcare facilities, or a micro-pump, for example. A negative-pressure supply may be housed within or used in conjunction with other components, such as sensors, processing units, alarm indicators, memory, databases, software, display devices, or user interfaces that further facilitate therapy. For example, in some embodiments, the negative-pressure source 104 may be combined with the controller 110 and other components into a therapy unit. A negative-pressure supply may also have one or more supply ports configured to facilitate coupling and de-coupling the negative-pressure supply to one or more distribution components.

The tissue interface 108 can be generally adapted to contact a tissue site. The tissue interface 108 may be partially or fully in contact with the tissue site. If the tissue site is a wound, for example, the tissue interface 108 may partially or completely fill the wound, or may be placed over the wound. The tissue interface 108 may take many forms, and may have many sizes, shapes, or thicknesses depending on a variety of factors, such as the type of treatment being implemented or the nature and size of a tissue site. For example, the size and shape of the tissue interface 108 may be adapted to the contours of deep and irregular shaped tissue sites. Moreover, any or all of the surfaces of the tissue interface 108 may have projections or an uneven, course, or jagged profile that can induce strains and stresses on a tissue site, which can promote granulation at the tissue site.

In some embodiments, the tissue interface 108 may include a manifold. A "manifold" in this context generally includes any substance or structure providing a plurality of pathways adapted to collect or distribute fluid across a tissue site under pressure. For example, a manifold may be adapted to receive negative pressure from a source and distribute negative pressure through multiple apertures across a tissue site, which may have the effect of collecting fluid from across a tissue site and drawing the fluid toward the source. In some embodiments, the fluid path may be reversed or a secondary fluid path may be provided to facilitate delivering fluid across a tissue site.

The tissue interface 108 may include either or both of hydrophobic and hydrophilic materials. In an example in which the tissue interface 108 may be hydrophilic, the tissue interface 108 may also wick fluid away from a tissue site, while continuing to distribute negative pressure to the tissue site. The wicking properties of the tissue interface 108 may draw fluid away from a tissue site by capillary flow or other wicking mechanisms. An example of a hydrophilic foam is a polyvinyl alcohol, open-cell foam such as V.A.C. WHITE-FOAM™ Dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

The tissue interface 108 may further promote granulation at a tissue site when pressure within the sealed therapeutic environment is reduced. For example, any or all of the surfaces of the tissue interface 108 may have an uneven, coarse, or jagged profile that can induce microstrains and stresses at a tissue site if negative pressure is applied through the tissue interface 108.

In some embodiments, the tissue interface 108 may also be constructed from one or more bioresorbable materials. Suitable bioresorbable materials may include, without limitation, a polymeric blend of polylactic acid (PLA) and polyglycolic acid (PGA). The polymeric blend may also include without limitation polycarbonates, polyfumarates, and capralactones.

In some embodiments, the cover 106 may provide a bacterial barrier and protection from physical trauma. The cover 106 may also be constructed from a material that can reduce evaporative losses and provide a fluid seal between two components or two environments, such as between a therapeutic environment and a local external environment. The cover 106 may be, for example, an elastomeric film or membrane that can provide a seal adequate to maintain a negative pressure at a tissue site for a given negative-pressure source. The cover 106 may have a high moisture-vapor transmission rate (MVTR) in some applications. For example, the MVTR may be at least 250 grams per square meter per twenty-four hours in some embodiments, measured using an upright cup technique according to ASTM E96/E96M Upright Cup Method at 38° C. and 10% relative humidity (RH). In some embodiments, an MVTR up to 5,000 grams per square meter per twenty-four hours may provide may provide effective breathability and mechanical properties. In some example embodiments, the cover 106 may be a polymer drape, such as a polyurethane film, that is permeable to water vapor but impermeable to liquid. Such drapes typically have a thickness in the range of 25-50 microns. For permeable materials, the permeability generally should be low enough that a desired negative pressure may be maintained.

An attachment device may be used to attach the cover 106 to an attachment surface, such as undamaged epidermis, a gasket, or another cover. The attachment device may take many forms. For example, an attachment device may be a medically-acceptable, pressure-sensitive adhesive that extends about a periphery, a portion, or an entire sealing member. In some embodiments, for example, some or all of the cover 106 may be coated with an acrylic adhesive having a coating weight between 25-65 grams per square meter (g.s.m.). Thicker adhesives, or combinations of adhesives, may be applied in some embodiments to improve the seal and reduce leaks. Other example embodiments of an attachment device may include a double-sided tape, paste, hydrocolloid, hydrogel, silicone gel, or organogel.

A controller, such as the controller 110, may be a microprocessor or computer programmed to operate one or more components of the therapy system 100, such as the negative-pressure source 104. In some embodiments, for example, the controller 110 may be a microcontroller, which generally comprises an integrated circuit containing a processor core and a memory programmed to directly or indirectly control one or more operating parameters of the therapy system 100. Operating parameters may include the power applied to the negative-pressure source 104, the pressure generated by the negative-pressure source 104, or the pressure distributed to the tissue interface 108, for example. The controller 110 is also preferably configured to receive one or more input signals, such as a feedback signal, and programmed to modify one or more operating parameters based on the input signals.

Sensors, such as the first sensor 120 and the second sensor 122, are generally known in the art as any apparatus operable to detect or measure a physical phenomenon or property, and generally provide a signal indicative of the phenomenon or property that is detected or measured. For example, the first sensor 120 and the second sensor 122 may be configured to measure one or more operating parameters of the therapy system 100. In some embodiments, the first sensor 120 may be a transducer configured to measure pressure in a pneumatic pathway and convert the measurement to a signal indicative of the pressure measured. In some embodiments, for example, the first sensor 120 may be a piezoresistive strain gauge. The second sensor 122 may optionally measure operating parameters of the negative-pressure source 104, such as the voltage or current, in some embodiments. Preferably, the signals from the first sensor 120 and the second sensor 122 are suitable as an input signal to the controller 110, but some signal conditioning may be appropriate in some embodiments. For example, the signal may need to be filtered or amplified before it can be processed by the controller 110. Typically, the signal is an electrical signal, but may be represented in other forms, such as an optical signal.

The container 112 is representative of a container, canister, pouch, or other storage component, which can be used to manage exudates and other fluids withdrawn from a tissue site. In many environments, a rigid container may be preferred or required for collecting, storing, and disposing of fluids. In other environments, fluids may be properly disposed of without rigid container storage, and a re-usable container could reduce waste and costs associated with negative-pressure therapy.

The solution source 114 may also be representative of a container, canister, pouch, bag, or other storage component, which can provide a solution for instillation therapy. Compositions of solutions may vary according to a prescribed therapy, but examples of solutions that may be suitable for some prescriptions include hypochlorite-based solutions, silver nitrate (0.5%), sulfur-based solutions, biguanides, cationic solutions, and isotonic solutions.

In operation, the tissue interface 108 may be placed within, over, on, or otherwise proximate to a tissue site. The cover 106 may be placed over the tissue interface 108 and sealed to an attachment surface near the tissue site. For example, the cover 106 may be sealed to undamaged epidermis peripheral to a tissue site. Thus, the dressing 102 can provide a sealed therapeutic environment proximate to a tissue site, substantially isolated from the external environment, and the negative-pressure source 104 can reduce the pressure in the sealed therapeutic environment. Negative pressure applied across the tissue site through the tissue interface 108 in the sealed therapeutic environment can induce macrostrain and microstrain in the tissue site, as well as remove exudates and other fluids from the tissue site, which can be collected in container 112.

The fluid mechanics of using a negative-pressure source to reduce pressure in another component or location, such as within a sealed therapeutic environment, can be mathematically complex. However, the basic principles of fluid mechanics applicable to negative-pressure therapy and instillation are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a source of negative pressure or further away from a source of positive pressure. Conversely, the term "upstream" implies something relatively further away from a source of negative pressure or closer to a source of positive pressure. Similarly, it may be convenient to describe certain features in terms of fluid "inlet" or "outlet" in such a frame of reference. This orientation is generally presumed for purposes of describing various features and components herein. However, the fluid path may also be reversed in some applications (such as by substituting a positive-pressure source for a negative-pressure source) and this descriptive convention should not be construed as a limiting convention.

"Negative pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

Figure 2:
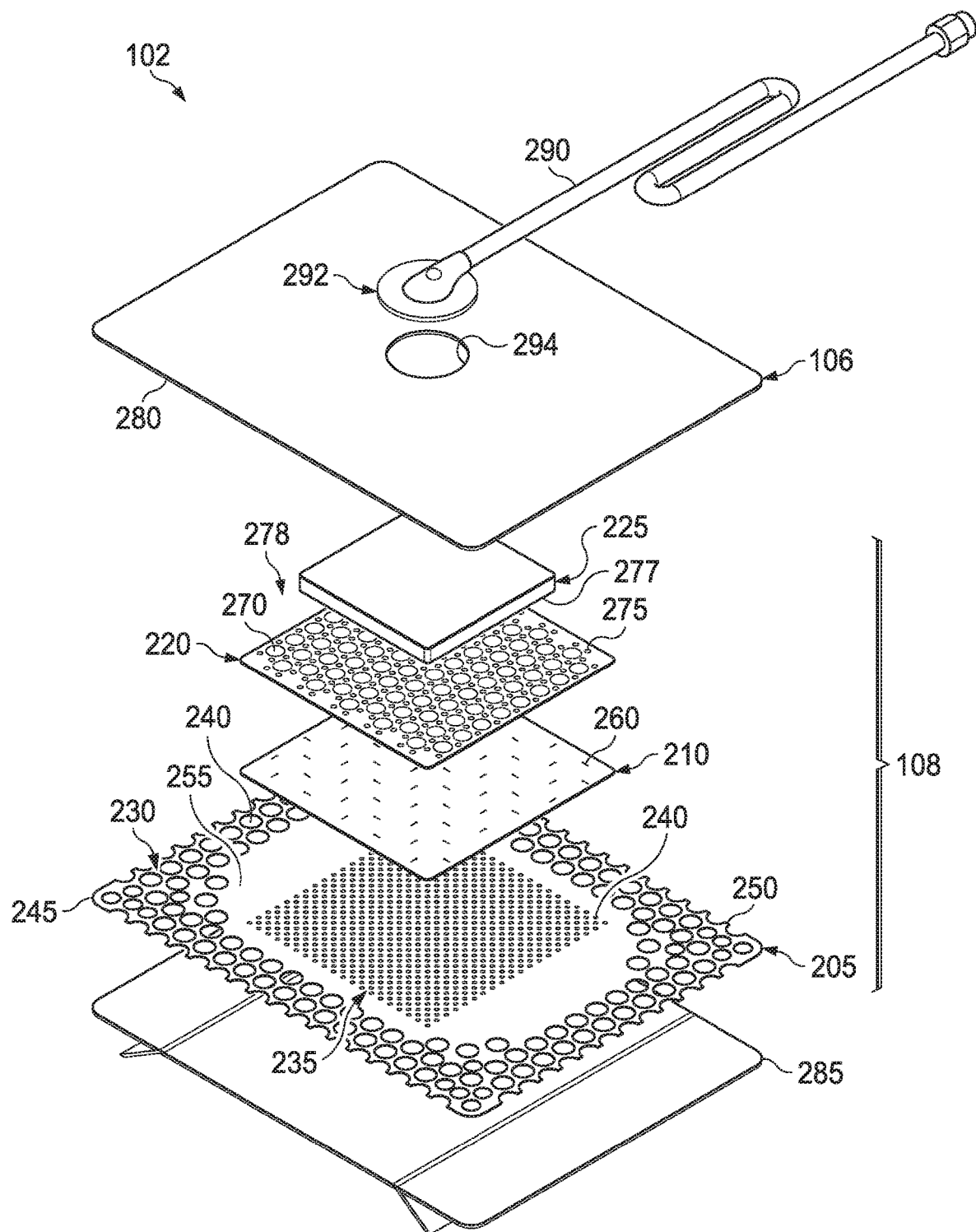
FIG. 2 is an assembly view of an example of a dressing illustrating additional details that may be associated with some example embodiments of the therapy system of FIG. 1.

FIG. 2 is an assembly view of an example of the dressing 102 of FIG. 1, illustrating additional details that may be associated with some embodiments in which the tissue interface 108 comprises more than one layer. In the example of FIG. 2, the tissue interface 108 comprises a first layer 205, a second layer 210, a third layer 220, and a fourth layer 225. In some embodiments, the first layer 205 may be disposed adjacent to the second layer 210, and the third layer 220 may be disposed adjacent to the second layer 210 opposite the first layer 205. Additionally, the fourth layer 225 may be disposed adjacent to the third layer 220 opposite the second layer 210. For example, the first layer 205, the second layer 210, the third layer 220, and the fourth layer 225 may be stacked so that the first layer 205 is in contact with the second layer 210, the second layer 210 is in contact with the first layer 205 and the third layer 220, and the third layer 220 is in contact with the second layer 210 and the fourth layer 225. One or more of the first layer 205, the second layer 210, the third layer 220, and the fourth layer 225 may also be bonded to an adjacent layer in some embodiments. While the overall dressing 102, including the layers of the tissue interface 108, is shown in FIG. 2 to have substantially a square shape, the dressing 102 and included layers may be any number of different shapes, based on the particular anatomical needs of a tissue site. For example, the dressing 102 and included layers may have a square, rectangular, oval, circular, hexagonal, or other shape. Additionally, the dressing 102 may further include three-dimensional forms that may be welded and shaped to address needs of specific types of tissue sites, such as breasts or post-amputation wounds.

The first layer 205 may be a sealing layer comprising or consisting essentially of a soft, tacky material suitable for providing a fluid seal with a tissue site, and may have a substantially flat surface. For example, the first layer 205 may comprise, without limitation, a silicone gel, a soft silicone, hydrocolloid, hydrogel, polyurethane gel, polyolefin gel, hydrogenated styrenic copolymer gel, a foamed gel, a soft closed cell foam such as polyurethanes and polyolefins coated with an adhesive, polyurethane, polyolefin, or hydrogenated styrenic copolymers. In some embodiments, the first layer 205 may be in the form of a film, and may have a thickness between about 200 microns (Mm) and about 1000 microns (Mm). In some embodiments, the first layer 205 may have a hardness between about 5 Shore OO and about 80 Shore OO. Further, the first layer 205 may be comprised of hydrophobic or hydrophilic materials.

In some embodiments, the first layer 205 may be a hydrophobic-coated material. For example, the first layer 205 may be formed by coating a spaced material, such as, for example, woven, nonwoven, molded, or extruded mesh with a hydrophobic material. The hydrophobic material for the coating may be a soft silicone, for example.

The first layer 205 may have a periphery 230 surrounding or around an interior portion 235, and apertures 240 disposed through the periphery 230 and the interior portion 235. The interior portion 235 may correspond to a surface area of the second layer 210 in some examples. The first layer 205 may also have corners 245 and edges 250. The corners 245 and the edges 250 may be part of the periphery 230. The first layer 205 may have an interior border 255 around the interior portion 235, disposed between the interior portion 235 and the periphery 230. The interior border 255 may be substantially free of the apertures 240, as illustrated in the example of FIG. 2. In some examples, as illustrated in FIG. 2, the interior portion 235 may be symmetrical and centrally disposed in the first layer 205.

The apertures 240 may be formed by cutting or by application of local RF or ultrasonic energy, for example, or by other suitable techniques for forming an opening. The apertures 240 may have a uniform distribution pattern, or may be randomly distributed on the first layer 205. The apertures 240 in the first layer 205 may have many shapes, including circles, squares, stars, ovals, polygons, slits, complex curves, rectilinear shapes, triangles, for example, or may have some combination of such shapes.

Each of the apertures 240 may have uniform or similar geometric properties. For example, in some embodiments, each of the apertures 240 may be circular apertures, having substantially the same diameter. In some embodiments, the diameter of each of the apertures 240 may be between about 1 millimeter to about 50 millimeters. In other embodiments, the diameter of each of the apertures 240 may be between about 1 millimeter to about 20 millimeters.

In other embodiments, geometric properties of the apertures 240 may vary. For example, the diameter of the apertures 240 may vary depending on the position of the apertures 240 in the first layer 205, as illustrated in FIG. 2. In some embodiments, the diameter of the apertures 240 in the periphery 230 of the first layer 205 may be larger than the diameter of the apertures 240 in the interior portion 235 of the first layer 205. For example, in some embodiments, the apertures 240 disposed in the periphery 230 may have a diameter between about 9.8 millimeters to about 10.2 millimeters. In some embodiments, the apertures 240 disposed in the corners 245 may have a diameter between about 7.75 millimeters to about 8.75 millimeters. In some embodiments, the apertures 240 disposed in the interior portion 235 may have a diameter between about 1.8 millimeters to about 2.2 millimeters.

At least one of the apertures 240 in the periphery 230 of the first layer 205 may be positioned at the edges 250 of the periphery 230, and may have an interior cut open or exposed at the edges 250 that is in fluid communication in a lateral direction with the edges 250. The lateral direction may refer to a direction toward the edges 250 and in the same plane as the first layer 205. As shown in the example of FIG. 2, the apertures 240 in the periphery 230 may be positioned proximate to or at the edges 250 and in fluid communication in a lateral direction with the edges 250. The apertures 240 positioned proximate to or at the edges 250 may be spaced substantially equidistant around the periphery 230 as shown in the example of FIG. 2. Alternatively, the spacing of the apertures 240 proximate to or at the edges 250 may be irregular.

The second layer 210 may comprise or consist essentially of a means for controlling or managing fluid flow. In some embodiments, the second layer 210 may comprise or consist essentially of a liquid-impermeable, elastomeric material. For example, the second layer 210 may comprise or consist essentially of a non-porous polymer film. The second layer 210 may also have a smooth or matte surface texture in some embodiments. A glossy or shiny finish better or equal to a grade B3 according to the SPI (Society of the Plastics Industry) standards may be particularly advantageous for some applications. In some embodiments, variations in surface height may be limited to acceptable tolerances. For example, the surface of the second layer may have a substantially flat surface, with height variations limited to 0.2 millimeters over a centimeter.

In some embodiments, the second layer 210 may be hydrophobic. The hydrophobicity of the second layer 210 may vary, but may have a contact angle with water of at least ninety degrees in some embodiments. In some embodiments, the second layer 210 may have a contact angle with water of no more than 150 degrees. For example, in some embodiments, the contact angle of the second layer 210 may be in a range of at least 90 degrees to about 120 degrees, or in a range of at least 120 degrees to 150 degrees. Water contact angles can be measured using any standard apparatus. Although manual goniometers can be used to visually approximate contact angles, contact angle measuring instruments can often include an integrated system involving a level stage, liquid dropper such as a syringe, camera, and software designed to calculate contact angles more accurately and precisely, among other things. Non-limiting examples of such integrated systems may include the FTA125, FTA200, FTA2000, and FTA4000 systems, all commercially available from First Ten Angstroms, Inc., of Portsmouth, Va., and the DTA25, DTA30, and DTA100 systems, all commercially available from Kruss GmbH of Hamburg, Germany. Unless otherwise specified, water contact angles herein are measured using deionized and distilled water on a level sample surface for a sessile drop added from a height of no more than 5 cm in air at 20-25° C. and 20-50% relative humidity. Contact angles reported herein represent averages of 5-9 measured values, discarding both the highest and lowest measured values. The hydrophobicity of the second layer 210 may be further enhanced with a hydrophobic coating of other materials, such as silicones and fluorocarbons, either as coated from a liquid or plasma coated.

The second layer 210 may also be suitable for welding to other layers. For example, the second layer 210 may be adapted for welding to other film layers using heat, radio frequency (RF) welding, or other methods to generate heat such as ultrasonic welding. RF welding may be particularly suitable for more polar materials, such as polyurethane, polyamides, polyesters and acrylates. Sacrificial polar interfaces may be used to facilitate RF welding of less polar film materials such as polyethylene.

The area density of the second layer 210 may vary according to a prescribed therapy or application. In some embodiments, an area density of less than 40 grams per square meter may be suitable, and an area density of about 20-30 grams per square meter may be particularly advantageous for some applications.

In some embodiments, for example, the second layer 210 may comprise or consist essentially of a hydrophobic polymer, such as a polyethylene film. The simple and inert structure of polyethylene can provide a surface that interacts little, if any, with biological tissues and fluids, providing a surface that may encourage the free flow of liquids and low adherence, which can be particularly advantageous for many applications. Other suitable polymeric films include polyurethanes, acrylics, polyolefin (such as cyclic olefin copolymers), polyacetates, polyamides, polyesters, copolyesters, PEBAX block copolymers, thermoplastic elastomers, thermoplastic vulcanizates, polyethers, polyvinyl alcohols, polypropylene, polymethylpentene, polycarbonate, styrenics, silicones, fluoropolymers, and acetates. A thickness between 20 microns and 100 microns may be suitable for many applications. Films may be clear, colored, or printed. More polar films suitable for laminating to a polyethylene film include polyamide, copolyesters, ionomers, and acrylics. To aid in the bond between a polyethylene and polar film, tie layers may be used, such as ethylene vinyl acetate, or modified polyurethanes. An ethyl methyl acrylate (EMA) film may also have suitable hydrophobic and welding properties for some configurations.

As illustrated in the example of FIG. 2, the second layer 210 may have one or more fluid restrictions 260, which can be distributed uniformly or randomly across the second layer 210. The fluid restrictions 260 may be bi-directional and pressure-responsive. For example, each of the fluid restrictions 260 generally may comprise or consist essentially of an elastic passage through the second layer 210 that is normally unstrained to substantially reduce liquid flow, and can expand or open in response to a pressure gradient. In some embodiments, the fluid restrictions 260 may comprise or consist essentially of perforations in the second layer 210. Perforations may be formed by removing material from the second layer 210. For example, perforations may be formed by cutting through the second layer 210, which may also deform the edges of the perforations in some embodiments.

In the absence of a pressure gradient across the perforations, the passages may be sufficiently small to form a seal or fluid restriction, which can substantially reduce or prevent liquid flow. Additionally or alternatively, one or more of the fluid restrictions 260 may be an elastomeric valve that is normally closed when unstrained to substantially prevent liquid flow, and can open in response to a pressure gradient. A fenestration in the second layer 210 may be a suitable valve for some applications. Fenestrations may also be formed by removing material from the second layer 210, but the amount of material removed and the resulting dimensions of the fenestrations may be up to an order of magnitude less than perforations, and may result in edges that are not deformed. Additionally, in some embodiments, perforations may be formed by mechanical slitting then controlled uni- and/or bi-axial stretching of the film material of the second layer 210.

For example, some embodiments of the fluid restrictions 260 may comprise or consist essentially of one or more slits, slots, or combinations of slits and slots in the second layer 210. In some examples, the fluid restrictions 260 may comprise or consist of linear slots having a length less than 4 millimeters and a width less than 1 millimeter. The length may be at least 2 millimeters, and the width may be at least 0.4 millimeters in some embodiments. A length of about 3 millimeters and a width of about 0.5 millimeters may be particularly suitable for many applications, and a tolerance of about 0.1 millimeter may also be acceptable. Such dimensions and tolerances may be achieved with a laser cutter, ultrasonics, or other heat means, for example. The linear slits or slots may be spaced apart by about 2 to 4 millimeters along their length and from side-to-side. Slots of such configurations may function as imperfect valves that substantially reduce liquid flow in a normally closed or resting state. For example, such slots may form a flow restriction without being completely closed or sealed. The slots can expand or open wider in response to a pressure gradient to allow increased liquid flow.

The third layer 220 generally comprises or consists essentially of a manifold or a manifold area, which provides a means for collecting or distributing fluid across the tissue interface 108 under pressure. For example, the third layer 220 may be adapted to receive negative pressure from a source and distribute negative pressure through multiple apertures across the tissue interface 108, which may have the effect of collecting fluid from across a tissue site and drawing the fluid toward the source. In some embodiments, the fluid path may be reversed or a secondary fluid path may be provided to facilitate delivering fluid, such as from a source of instillation solution, across the tissue interface 108.

In some embodiments, the third layer 220 may comprise or consist essentially of a film of fluid-impermeable material having bubbles. In some embodiments, the third layer 220 may comprise a film of transparent material. Polyurethane and polyethylene are examples of suitable fluid-impermeable materials for some applications of the third layer 220. In some embodiments, the bubbles may include raised formations, protrusions, spacers, or standoffs. For example, the third layer 220 may include bubbles in the form of blisters 270, which may extend above or below a reference plane of the third layer 220. Within each of the blisters 270 may be an empty cavity that may be open to the surrounding environment. For example, portions of a film of fluid-impermeable material that forms the third layer 220 may be shaped or formed to include the blisters 270. In some embodiments, the blisters 270 may be in the form of small vacuum-formed regions of the film of the third layer 220. In some embodiments, each individual blister of the blisters 270 may be dome-shaped or hemispherically-shaped. Additionally or alternatively, the blisters 270 may be in the form of raised formations having different shapes, such as generally conical, cylindrical, tubular having a flattened or hemispherical end, or geodesic. In some embodiments, the third layer 220 may be positioned in the tissue interface 108 so that the blisters 270 protrude towards or face the second layer 210. The pitch and spacing of the blisters 270 may differ across the surface of the third layer 220. For example, the blisters 270 may be further spaced apart in a center region of the third layer 220. The third layer 220 may further include apertures 275 to allow fluid transfer through the film. The blisters 270 may assist with enabling the third layer 220 to function as the core manifolding layer of the tissue interface 108. The surface area of the third layer 220, including blisters 270 and/or apertures 275, may define a manifold area of the third layer 220 and tissue interface 108.

In some additional embodiments, the third layer 220 may include bubbles in the form of air pockets, which may be either open or closed. For example, the bubbles may include closed cells, which may be in the form of sealed air pockets. Additionally or alternatively, the third layer 220 may also include ridges, grooves, or other structural features having sufficient rigidity to maintain their shape and form when applied as part of the tissue interface 108.

The thickness of the third layer 220 may also vary according to needs of a prescribed therapy. For example, the thickness of the third layer 220 may be decreased to relieve stress on other layers and to reduce tension on peripheral tissue. The thickness of the third layer 220 can also affect the conformability of the third layer 220. In some embodiments, the third layer 220 may comprise a film having a thickness in a range of about 20 to 500 micrometers. For example, the third layer 220 may comprise a film having a thickness of approximately 250 micrometers with blisters 270 having a diameter of between 0.5 mm and 2.0 mm.

The fourth layer 225 may also comprise or consist essentially of a manifold or manifold layer. For example, the fourth layer 225 may be adapted to receive negative pressure from a source and distribute negative pressure through multiple apertures across the tissue interface 108, which may have the effect of collecting fluid from across a tissue site and drawing the fluid toward the source.

In some illustrative embodiments, the fourth layer 225 may comprise a plurality of pathways, which can be interconnected to improve distribution or collection of fluids. In some embodiments, the fourth layer 225 may comprise or consist essentially of a porous material having interconnected fluid pathways. For example, cellular foam, open-cell foam, reticulated foam, porous tissue collections, and other porous material such as gauze or felted mat generally include pores, edges, and/or walls adapted to form interconnected fluid channels. Liquids, gels, and other foams may also include or be cured to include apertures and fluid pathways. In some embodiments, the fourth layer 225 may additionally or alternatively comprise projections that form interconnected fluid pathways. For example, the fourth layer 225 may be molded to provide surface projections that define interconnected fluid pathways. Any or all of the surfaces of the fourth layer 225 may have an uneven, coarse, or jagged profile.

In some embodiments, the fourth layer 225 may comprise or consist essentially of a reticulated foam having pore sizes and free volume that may vary according to needs of a prescribed therapy. For example, a reticulated foam having a free volume of at least 90% may be suitable for many therapy applications, and a foam having an average pore size in a range of 400-600 microns (40-50 pores per inch) may be particularly suitable for some types of therapy. The tensile strength of the fourth layer 225 may also vary according to needs of a prescribed therapy. For example, the tensile strength of a foam may be increased for instillation of topical treatment solutions. The 25% compression load deflection of the fourth layer 225 may be at least 0.35 pounds per square inch, and the 65% compression load deflection may be at least 0.43 pounds per square inch. In some embodiments, the tensile strength of the fourth layer 225 may be at least 10 pounds per square inch. The fourth layer 225 may have a tear strength of at least 2.5 pounds per inch. In some embodiments, the first layer 225 may be a foam comprised of polyols such as polyester or polyether, isocyanate such as toluene diisocyanate, and polymerization modifiers such as amines and tin compounds. In one non-limiting example, the fourth layer 225 may be a reticulated polyurethane ether foam such as used in GRANUFOAM™ dressing or V.A.C. VERAFLO™ dressing, both available from KCI of San Antonio, Tex.

The thickness of the fourth layer 225 may also vary according to needs of a prescribed therapy. For example, the thickness of the fourth layer 225 may be decreased to relieve stress on other layers and to reduce tension on peripheral tissue. The thickness of the fourth layer 225 can also affect the conformability of the fourth layer 225. In some embodiments, a thickness in a range of about 2 millimeters to 10 millimeters may be suitable. In some embodiments, the fourth layer 225 may be partially or completely opaque, or otherwise be such that the fourth layer 225 may block at least a portion of light passage.

In the example embodiment of FIG. 2, the fourth layer 225 may be sized and positioned so that the edges of the fourth layer 225 are placed inboard of the edges of the third layer 220. For example, the fourth layer 225 may have a cross-section parallel to the reference plane of the third layer, and the area of the cross-section is less than an area of a side of the third layer 220. In some embodiments, the fourth layer 225 may have a first, or lower, side adapted to be positioned against the third layer 220 and a second, or upper, side that may be generally parallel to the first side of the fourth layer 225. The first side and the second side of the fourth layer 225 may each have a surface area that is substantially equal. The surface area of each of the first side and the second side of the fourth layer 225 may be less than the surface area of the side of the third layer 220 positioned adjacent to the first side of the fourth layer 225.

In some embodiments, the fourth layer 225 may have a first side defining a face 277 having a contact area, which may correspond to a portion of the manifold area of the third layer 220. In some embodiments, the contact area of the face 277 may be less than or smaller than the manifold area of the third layer 220, and also the areas of the other layers of the tissue interface 108. For example, the contact area of the fourth layer 225 may be approximately greater than or equal to 30% of the manifold area of the third layer 220. A portion of the manifold area of the third layer 220, or manifold margin 278, may not be covered by the fourth layer 225. As such, in some embodiments, a portion of an upper surface of the third layer 220 may be exposed to or in contact with the cover 106, and may also allow a user to view the portion of the third layer 220 through the cover 106.

In some embodiments, a manifold area of the third layer 220, and likewise of the tissue interface 108, may be defined by or correspond to the surface area of an upper or lower side of the third layer 220. As shown in FIG. 2, the contact area associated with the face 277 of the fourth layer 225 may be positioned against or adjacent to a central portion of the manifold area of the third layer 220. In such embodiments, the fourth layer 225 may provide an enhanced manifolding capability to the central portion(s) of the manifold area of the third layer 220. This enhanced manifolding to the central portion(s) of the manifold area of the third layer 220 and tissue interface 108 may be advantageous as the central part of the tissue interface 108 may generally be aligned over the tissue site, such as a wound. Additionally, by including a fourth layer 225 that does not extend to the edges of the manifold area defined by the third layer 220, and thus the tissue interface 108, interference between the fourth layer 225 and edges of a tissue site, such as a peri-wound area, may be minimized or avoided.

In the example of FIG. 2, the dressing 102 may further include an attachment device, such as an adhesive 280. The adhesive 280 may be, for example, a medically-acceptable, pressure-sensitive adhesive that extends about a periphery, a portion, or the entire cover 106. In some embodiments, for example, the adhesive 280 may be an acrylic adhesive having a coating weight between 25-65 grams per square meter (g.s.m.). Thicker adhesives, or combinations of adhesives, may be applied in some embodiments to improve the seal and reduce leaks. In some embodiments, such a layer of the adhesive 280 may be continuous or discontinuous. Discontinuities in the adhesive 280 may be provided by apertures or holes (not shown) in the adhesive 280. The apertures or holes in the adhesive 280 may be formed after application of the adhesive 280 or by coating the adhesive 280 in patterns on a carrier layer such as a side of the cover 106. Apertures or holes in the adhesive 280 may also be sized to enhance the MVTR of the dressing 102 in some example embodiments.

As illustrated in the example of FIG. 2, in some embodiments, the dressing 102 may include a release liner 285 to protect the adhesive 280 prior to use. The release liner 285 may also provide stiffness to assist with, for example, deployment of the dressing 102. The release liner 285 may be, for example, a casting paper, a film, or polyethylene. Further, in some embodiments, the release liner 285 may be a polyester material such as polyethylene terephthalate (PET) or similar polar semi-crystalline polymer. The use of a polar semi-crystalline polymer for the release liner 285 may substantially preclude wrinkling or other deformation of the dressing 102. For example, the polar semi-crystalline polymer may be highly orientated and resistant to softening, swelling, or other deformation that may occur when brought into contact with components of the dressing 102 or when subjected to temperature or environmental variations, or sterilization. Further, a release agent may be disposed on a side of the release liner 285 that is configured to contact the first layer 205. For example, the release agent may be a silicone coating and may have a release factor suitable to facilitate removal of the release liner 285 by hand and without damaging or deforming the dressing 102. In some embodiments, the release agent may be a fluorocarbon or a fluorosilicone, for example. In other embodiments, the release liner 285 may be uncoated or otherwise used without a release agent.

FIG. 2 also illustrates one example of a fluid conductor 290 and a dressing interface 292. As shown in the example of FIG. 2, the fluid conductor 290 may be a flexible tube, which can be fluidly coupled on one end to the dressing interface 292. The dressing interface 292 may be an elbow connector, as shown in the example of FIG. 2, which can be placed over an aperture 294 in the cover 106 to provide a fluid path between the fluid conductor 290 and the tissue interface 108. In some embodiments, the fluid conductor 290 may also include a fluid delivery conduit for use with instillation therapy. Further, in some embodiments, the dressing interface 292 may include multiple fluid conduits, such as a conduit for communicating negative pressure and a fluid delivery conduit. For example, the dressing interface 292 may be a V.A.C. VERAT.R.A.C.™ Pad.

Figure 3:
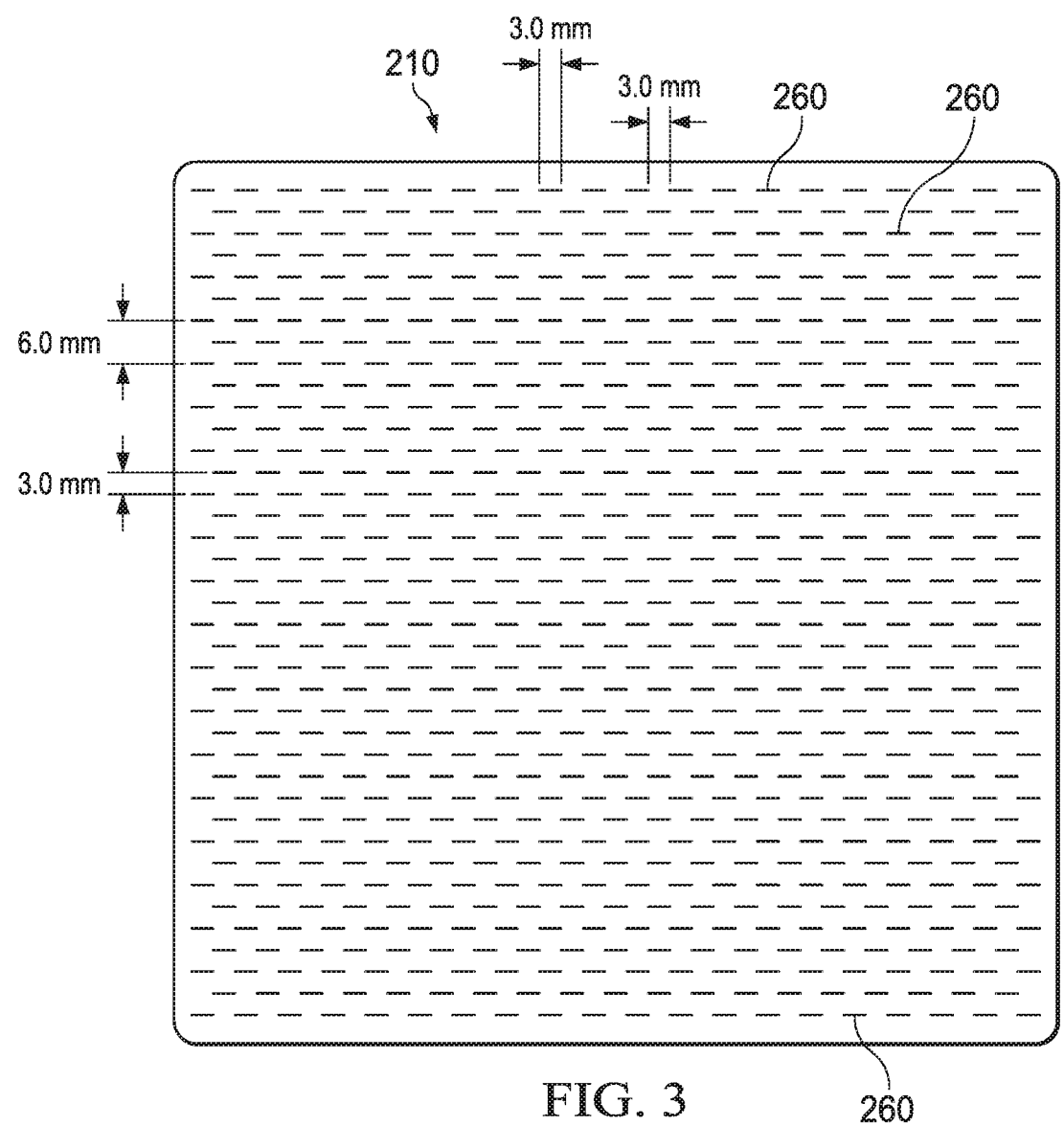
FIG. 3 is a schematic view of an example configuration of fluid restrictions in a layer that may be associated with some embodiments of the dressing of FIG. 2.

FIG. 3 is a schematic view of an example of the second layer 210, illustrating additional details that may be associated with some embodiments. As illustrated in the example of FIG. 3, the fluid restrictions 260 may each consist essentially of one or more linear slots having a length of about 3 millimeters. FIG. 3 additionally illustrates an example of a uniform distribution pattern of the fluid restrictions 260. In FIG. 3, the fluid restrictions 260 are substantially coextensive with the second layer 210 and are distributed across the second layer 210 in a grid of parallel rows and columns, in which the slots are also mutually parallel to each other. In some embodiments, the rows may be spaced about 3 millimeters on center, and the fluid restrictions 260 within each of the rows may be spaced about 3 millimeters on center as illustrated in the example of FIG. 3. The fluid restrictions 260 in adjacent rows may be aligned or offset. For example, adjacent rows may be offset, as illustrated in FIG. 3, so that the fluid restrictions 260 are aligned in alternating rows and separated by about 6 millimeters. The spacing of the fluid restrictions 260 may vary in some embodiments to increase the density of the fluid restrictions 260 according to therapeutic requirements.

Figure 4:
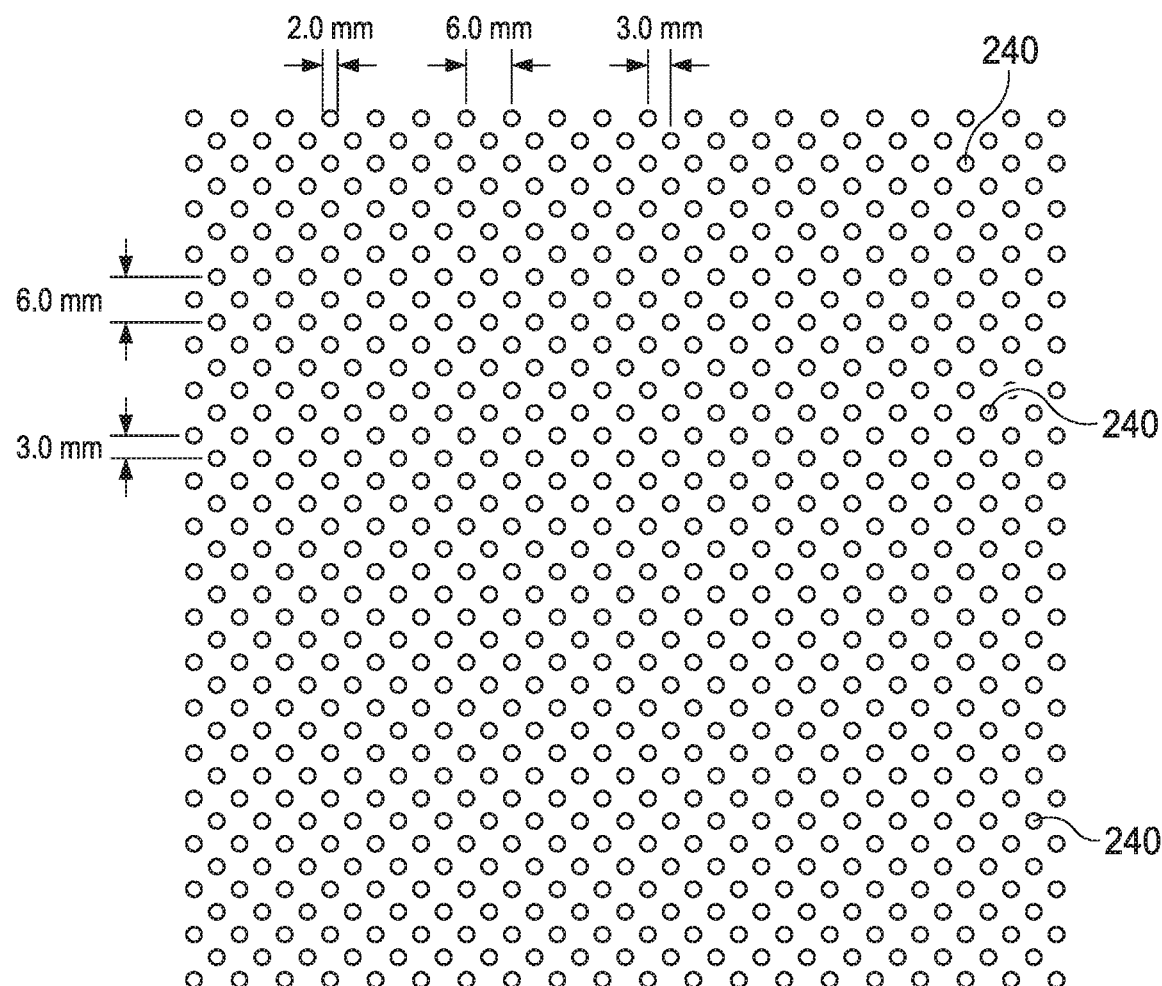
FIG. 4 is a schematic view of an example configuration of apertures in another layer, illustrating additional details that may be associated with some embodiments of the dressing of FIG. 2.

FIG. 4 is a schematic view of an example configuration of the apertures 240, illustrating additional details that may be associated with some embodiments of the first layer 205. In some embodiments, the apertures 240 illustrated in FIG. 4 may be associated only with the interior portion 235. In the example of FIG. 4, the apertures 240 are generally circular and have a diameter of about 2 millimeters. FIG. 4 also illustrates an example of a uniform distribution pattern of the apertures 240 in the interior portion 235. In FIG. 4, the apertures 240 are distributed across the interior portion 235 in a grid of parallel rows and columns. Within each row and column, the apertures 240 may be equidistant from each other, as illustrated in the example of FIG. 4. FIG. 4 illustrates one example configuration that may be particularly suitable for many applications, in which the apertures 240 are spaced about 6 millimeters apart along each row and column, with a 3 millimeter offset.

Figure 5:
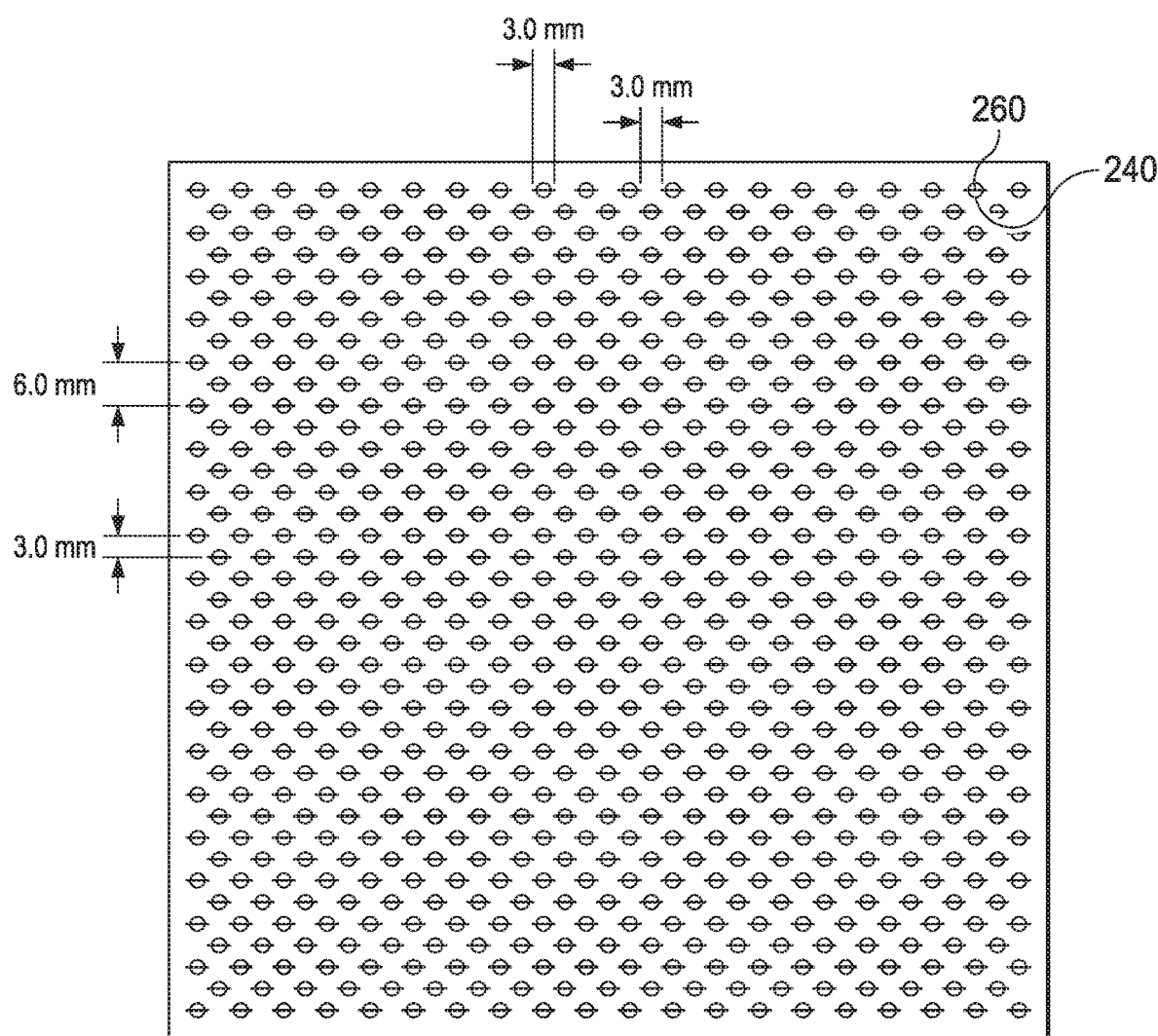
FIG. 5 is a schematic view of the example layer of FIG. 4 overlaid on the example layer of FIG. 3.

FIG. 5 is a schematic view of the example first layer 205 of FIG. 4 overlaid on the second layer 210 of FIG. 3, illustrating additional details that may be associated with some example embodiments of the tissue interface 108. For example, as illustrated in FIG. 5, the fluid restrictions 260 may be aligned, overlapping, in registration with, or otherwise fluidly coupled to the apertures 240 in some embodiments. In some embodiments, one or more of the fluid restrictions 260 may be registered with the apertures 240 only in the interior portion 235, or only partially registered with the apertures 240. The fluid restrictions 260 in the example of FIG. 5 are generally configured so that each of the fluid restrictions 260 is registered with only one of the apertures 240. In other examples, one or more of the fluid restrictions 260 may be registered with more than one of the apertures 240. For example, any one or more of the fluid restrictions 260 may be a perforation or a fenestration that extends across two or more of the apertures 240. Additionally or alternatively, one or more of the fluid restrictions 260 may not be registered with any of the apertures 240.

As illustrated in the example of FIG. 5, the apertures 240 may be sized to expose a portion of the second layer 210, the fluid restrictions 260, or both through the first layer 205. In some embodiments, each of the apertures 240 may be sized to expose no more than two of the fluid restrictions 260. In some examples, the length of each of the fluid restrictions 260 may be substantially equal to or less than the diameter of each of the apertures 240. In some embodiments, the average dimensions of the fluid restrictions 260 are substantially similar to the average dimensions of the apertures 240. For example, the apertures 240 may be elliptical in some embodiments, and the length of each of the fluid restrictions 260 may be substantially equal to the major axis or the minor axis. In some embodiments, though, the dimensions of the fluid restrictions 260 may exceed the dimensions of the apertures 240, and the size of the apertures 240 may limit the effective size of the fluid restrictions 260 exposed to the lower surface of the dressing 102.

Figure 6:
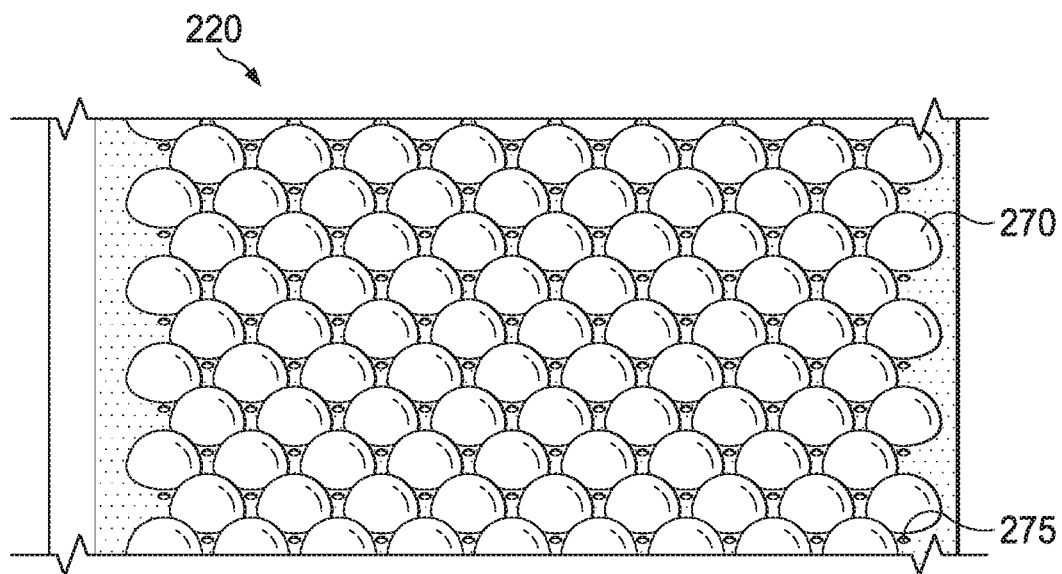
FIG. 6 is a perspective view of an example configuration of blisters in another layer that may be associated with some embodiments of the dressing of FIG. 2.

FIG. 6 is a perspective view of an example of the third layer 220, illustrating additional details that may be associated with some embodiments. As illustrated in the example of FIG. 6, the blisters 270 may be generally hemispherical and uniformly distributed in some embodiments.

Figure 7:
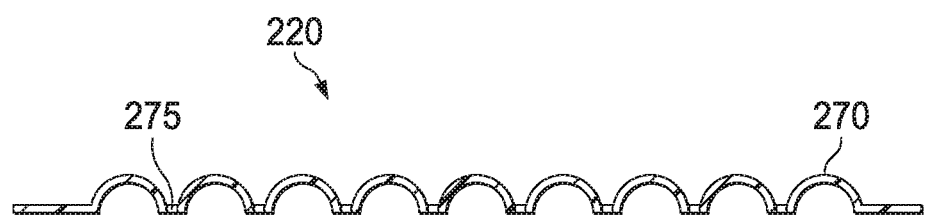
FIG. 7 is a section view illustrating additional details that may be associated with some embodiments of the layer of FIG. 6.

FIG. 7 is a section view of the third layer 220 of FIG. 6, illustrating additional details that may be associated with some embodiments. For example, the third layer 220 may be formed of a single sheet or film of fluid-impermeable material, which may have the blisters 270 and apertures 275 formed thereon. In some embodiments, the third layer 220 may be formed from a polyurethane material. The blisters 270 may be formed in the third layer 220 by applying a vacuum to the film of fluid-impermeable material of the third layer 220 to create the blisters 270. The blisters 270 may have dimensions that depend on the particular application of the dressing 102. For example, each of the blisters 270 may have a height between approximately 0.5 mm and 3.0 mm and may have a diameter between approximately 1.0 mm and 3.0 mm. In some embodiments, the blisters 270 may measure approximately 1.5 mm in height and approximately 1.5 mm in diameter. The distance between each of the blisters 270 may be between approximately 0.5 mm and 3.0 mm, and in some embodiments may have a spacing of approximately 2.0 mm.

As shown in FIG. 7, the apertures 275 may be formed in the portions of the third layer 220 that are between the blisters 270 and may extend through the film of fluid-impermeable material to permit fluids to flow through the third layer 220. The number of apertures 275 may vary depending on the type of negative pressure and instillation therapy to be provided by the therapy system 100. The apertures 275 may have different shapes, such as, for example, circular, elliptical, rectangular, or other irregular shape. Such apertures 275 may have a diameter, major axis, or length between about 0.5 mm and 2.0 mm. In some example embodiments, the apertures 275 may be formed by cutting or perforating, punching, or cutting using a laser or heat the fluid-impermeable material of the third layer 220.

In some embodiments of the dressing 102, one or more components of the dressing 102 may additionally be treated with an antimicrobial agent. For example, the first layer 205, the second layer 210, the third layer 220, and/or the fourth layer 225 may be coated with an antimicrobial agent. In some embodiments, the second layer 210 may comprise a polymer coated or mixed with an antimicrobial agent. In further embodiments, the third layer 220 may comprise films coated or mixed with an antimicrobial agent. In other examples, the cover 106, the fluid conductor 290, the dressing interface 292, or other portion of the dressing 102 may additionally or alternatively be treated with one or more antimicrobial agents. Suitable antimicrobial agents may include, for example, metallic silver, PHMB, iodine or its complexes and mixes such as povidone iodine, copper metal compounds, chlorhexidine, or some combination of these materials.

Individual components of the dressing 102 may be bonded or otherwise secured to one another with a solvent or non-solvent adhesive, or with thermal welding, for example, without adversely affecting fluid management. Further, the second layer 210 or the third layer 220 may be coupled to the border 255 of the first layer 205 in any suitable manner, such as with a weld or an adhesive, for example.

The cover 106, the first layer 205, the second layer 210, the third layer 220, the fourth layer 225, or various combinations may be assembled before application or in situ. For example, the cover 106 may be laminated to the fourth layer 225 and/or the third layer 220, and the second layer 210 may be laminated to the third layer 220 opposite the cover 106 in some embodiments. The first layer 205 may also be coupled to the second layer 210 opposite the third layer 220 in some embodiments. In some embodiments, one or more layers of the tissue interface 108 may be coextensive. For example, the third layer 220 may be coextensive with the second layer 210, as illustrated in the embodiment of FIG. 2. In some embodiments, the dressing 102 may be provided as a single, composite dressing. For example, the first layer 205 may be coupled to the cover 106 to enclose the second layer 210, the third layer 220, and the fourth layer 225, wherein the first layer 205 is configured to face a tissue site.

In additional embodiments, the dressing 102 may be provided with different combinations of the individual layers and components. For example, the tissue interface 108, such as the tissue interface 108 shown in FIG. 2, may be provided as a standalone product for applying to a tissue site. In some further embodiments, individual layers of the tissue interface 108 and the dressing 102 may be omitted. For example, in some embodiments, the tissue interface 108 may be provided with the second layer 210, the third layer 220, and fourth layer 225 positioned between the second layer 210 and the third layer 220. In such embodiments, the third layer 220 may be configured to include a fluid port for mating with a dressing interface, such as dressing interface 292.

In use, the release liner 285 (if included) may be removed to expose the first layer 205, which may be placed within, over, on, or otherwise proximate to a tissue site, particularly a surface tissue site and adjacent epidermis. The first layer 205, second layer 210, and third layer 220 may be interposed between the fourth layer 225 and the tissue site, which can substantially reduce or eliminate adverse interaction with the fourth layer 225. For example, the first layer 205 may be placed over a surface wound (including edges of the wound) and undamaged epidermis to prevent direct contact with the fourth layer 225. Treatment of a surface wound or placement of the dressing 102 on a surface wound includes placing the dressing 102 immediately adjacent to the surface of the body or extending over at least a portion of the surface of the body. Treatment of a surface wound does not include placing the dressing 102 wholly within the body or wholly under the surface of the body, such as placing a dressing within an abdominal cavity. In some applications, the interior portion 235 of the first layer 205 may be positioned adjacent to, proximate to, or covering a tissue site. In some applications, at least some portion of the second layer 210, the fluid restrictions 260, or both may be exposed to a tissue site through the first layer 205. The periphery 230 of the first layer 205 may be positioned adjacent to or proximate to tissue around or surrounding the tissue site. The first layer 205 may be sufficiently tacky to hold the dressing 102 in position, while also allowing the dressing 102 to be removed or re-positioned without trauma to the tissue site.

Removing the release liner 285 can also expose the adhesive 280, and the cover 106 may be attached to an attachment surface. For example, the cover 106 may be attached to epidermis peripheral to a tissue site, around the fourth layer 225, the third layer 220, and the second layer 210. The adhesive 280 may be in fluid communication with an attachment surface through the apertures 240 in at least the periphery 230 of the first layer 205 in some embodiments. The adhesive 280 may also be in fluid communication with the edges 250 through the apertures 240 exposed at the edges 250.

Once the dressing 102 is in the desired position, the adhesive 280 may be pressed through the apertures 240 to bond the dressing 102 to the attachment surface. The apertures 240 at the edges 250 may permit the adhesive 280 to flow around the edges 250 for enhancing the adhesion of the edges 250 to an attachment surface.

In some embodiments, apertures or holes in the first layer 205 may be sized to control the amount of the adhesive 280 in fluid communication with the apertures 240. For a given geometry of the corners 245, the relative sizes of the apertures 240 may be configured to maximize the surface area of the adhesive 280 exposed and in fluid communication through the apertures 240 at the corners 245. For example, as shown in FIG. 2, the edges 250 may intersect at substantially a right angle, or about 90 degrees, to define the corners 245. In some embodiments, the corners 245 may have a radius of about 10 millimeters. Further, in some embodiments, three of the apertures 240 having a diameter between about 7.75 millimeters to about 8.75 millimeters may be positioned in a triangular configuration at the corners 245 to maximize the exposed surface area for the adhesive 280. In other embodiments, the size and number of the apertures 240 in the corners 245 may be adjusted as necessary, depending on the chosen geometry of the corners 245, to maximize the exposed surface area of the adhesive 280. Further, the apertures 240 at the corners 245 may be fully housed within the first layer 205, substantially precluding fluid communication in a lateral direction exterior to the corners 245. The apertures 240 at the corners 245 being fully housed within the first layer 205 may substantially preclude fluid communication of the adhesive 280 exterior to the corners 245, and may provide improved handling of the dressing 102 during deployment at a tissue site. Further, the exterior of the corners 245 being substantially free of the adhesive 280 may increase the flexibility of the corners 245 to enhance comfort.

In some embodiments, the bond strength of the adhesive 280 may vary in different locations of the dressing 102. For example, the adhesive 280 may have a lower bond strength in locations adjacent to the first layer 205 where the apertures 240 are relatively larger, and may have a higher bond strength where the apertures 240 are smaller. Adhesive 280 with lower bond strength in combination with larger apertures 240 may provide a bond comparable to adhesive 280 with higher bond strength in locations having smaller apertures 240.

The geometry and dimensions of the tissue interface 108, the cover 106, or both may vary to suit a particular application or anatomy. For example, the geometry or dimensions of the tissue interface 108 and the cover 106 may be adapted to provide an effective and reliable seal against challenging anatomical surfaces, such as an elbow or heel, at and around a tissue site. Additionally or alternatively, the dimensions may be modified to increase the surface area for the first layer 205 to enhance the movement and proliferation of epithelial cells at a tissue site and reduce the likelihood of granulation tissue in-growth.

Thus, the dressing 102 in the example of FIG. 2 can provide a sealed therapeutic environment proximate to a tissue site, substantially isolated from the external environment, and the negative-pressure source 104 can reduce the pressure in the sealed therapeutic environment. The first layer 205 may provide an effective and reliable seal against challenging anatomical surfaces, such as an elbow or heel, at and around a tissue site. Further, the dressing 102 may permit re-application or re-positioning, to correct air leaks caused by creases and other discontinuities in the dressing 102, for example. The ability to rectify leaks may increase the efficacy of the therapy and reduce power consumption in some embodiments.

If not already configured, the dressing interface 292 may be disposed over the aperture 294 and attached to the cover 106. The fluid conductor 290 may be fluidly coupled to the dressing interface 292 and to the negative-pressure source 104.

Negative pressure applied through the tissue interface 108 can create a negative pressure differential across the fluid restrictions 260 in the second layer 210, which can open or expand the fluid restrictions 260 from their resting state. For example, in some embodiments in which the fluid restrictions 260 may comprise substantially closed fenestrations through the second layer 210, a pressure gradient across the fenestrations can strain the adjacent material of the second layer 210 and increase the dimensions of the fenestrations to allow liquid movement through them, similar to the operation of a duckbill valve. Opening the fluid restrictions 260 can allow exudate and other liquid movement through the fluid restrictions 260, through the apertures 275 of the third layer 220, and into the fourth layer 225 and the container 112. Changes in pressure can also cause the fourth layer 225 to expand and contract, and the third layer 220 as well as the interior border 255 of the first layer 205 may protect the epidermis from irritation caused by movement of the fourth layer 225. The third layer 220, the second layer 210, and the first layer 205 can also substantially reduce or prevent exposure of tissue to the fourth layer 225, which can inhibit growth of tissue into the fourth layer 225.

In some embodiments, the fourth layer 225 may be hydrophobic to minimize retention or storage of liquid in the dressing 102. In other embodiments, the fourth layer 225 may be hydrophilic. In an example in which the fourth layer 225 may be hydrophilic, the fourth layer 225 may also wick fluid away from a tissue site, while continuing to distribute negative pressure to the tissue site. The wicking properties of the fourth layer 225 may draw fluid away from a tissue site by capillary flow or other wicking mechanisms, for example. An example of a hydrophilic fourth layer 225 is a polyvinyl alcohol, open-cell foam such as V.A.C. WHITE-FOAM™ Dressing available from Kinetic Concepts, Inc. of San Antonio, Tex. Other hydrophilic foams may include those made from polyether. Other foams that may exhibit hydrophilic characteristics include hydrophobic foams that have been treated or coated to provide hydrophilicity.

If the negative-pressure source 104 is removed or turned-off, the pressure differential across the fluid restrictions 260 can dissipate, allowing the fluid restrictions 260 to move to their resting state and prevent or reduce the rate at which exudate or other liquid can return to the tissue site through the second layer 210.

In some applications, a filler may also be disposed between a tissue site and the first layer 205. For example, if the tissue site is a surface wound, a wound filler may be applied interior to the periwound, and the first layer 205 may be disposed over the periwound and the wound filler. In some embodiments, the filler may be a manifold, such as an open-cell foam. The filler may comprise or consist essentially of the same material as the fourth layer 225 in some embodiments.

Additionally or alternatively, instillation solution or other fluid may be distributed to the dressing 102, which can increase the pressure in the tissue interface 108. The increased pressure in the tissue interface 108 can create a positive pressure differential across the fluid restrictions 260 in the second layer 210, which can open or expand the fluid restrictions 260 from their resting state to allow the instillation solution or other fluid to be distributed to the tissue site.

Figure 8:
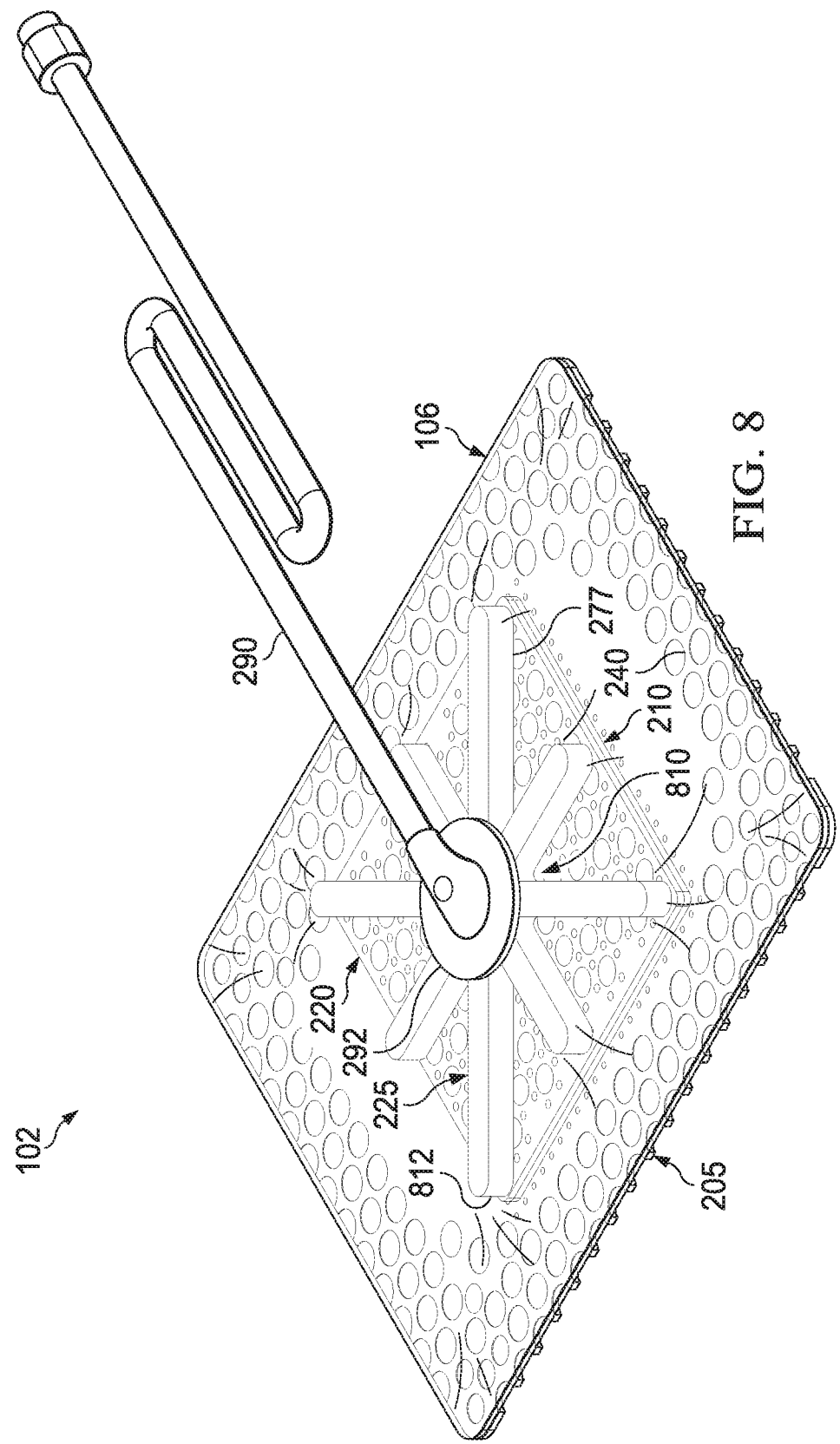
FIG. 8 is a schematic view of another example of a dressing illustrating additional details that may be associated with some example embodiments of the therapy system of FIG. 1.

FIG. 8 is a schematic diagram of another example of the dressing 102. While many of the components of the dressing 102 of FIG. 8 may be the same as or similar to those of the dressing 102 of FIG. 2, differences with respect to the individual layers of the dressings may be identified. For example, the dressing 102 of FIG. 8 may include a tissue interface 108 having a fourth layer 225 that is of a different shape and/or configuration than the fourth layer 225 of FIG. 2. As shown in FIG. 8, in some embodiments, the fourth layer 225 may be in the shape of a star or other similar shape having a central region 810 and one or more appendages, such as radial legs 812 or regions, extending from the central region 810. The fourth layer 225 may have an approximate thickness of between 4 mm and 10 mm, and in some embodiments approximately 6 mm. The face 277 of the fourth layer 225 may define a contact area that is shaped by, defined by, or includes the central region 810 and/or one or more appendages, such as the radial legs 812. The fourth layer 225 may be placed above or against a manifold area of the third layer 220, and may provide enhanced manifolding to the portions of the manifold area of the third layer 220 placed against the contact area defined by the central region 810 and radial legs 812 of the fourth layer 225. The size of the contact area provided by the central region 810 and the radial legs 812 of the fourth layer 225 may be based on the dimensions of the other layers, such as the third layer 220, in the tissue interface 108. In some embodiments, the contact area provided by the fourth layer 225 may be approximately greater than or equal to 30% of the manifold area of the third layer 220.

As discussed with respect to FIG. 2, the perimeter of the third layer 220 may define the borders of a manifold area of the tissue interface 108. In some embodiments, the radial legs 812 of the fourth layer 225 may substantially extend to the edges of the third layer 220 and to the borders of the manifold area. For example, the radial legs 812 of the fourth layer 225 may extend approximately 90% of the length and/or width of the manifold area of the third layer 220. Stated another way, in some embodiments, a margin of about 10% of length and/or width dimensions of the manifold area of the third layer 220 may be included beyond the extended area of the radial legs 812. Portions of the third layer 220 within the manifold area may not be placed against or covered by a portion of the contact area of the fourth layer 225, and thus portions of the upper side of the third layer 220 within the manifold area may be exposed to the cover 106 of the dressing 102. The portions of the third layer 220 not covered by the central region 810 or radial legs 812 of the fourth layer 225 may remain visible to a user looking upon the dressing 102. Furthermore, since in some embodiments of the tissue interface 108, the third layer 220, second layer 210, and first layer 205 may each comprise one or more transparent material(s), a portion or portions of the tissue site may remain visible to a user throughout the wear duration of the dressing 102. The shape and configuration of the fourth layer 225 of FIG. 8 may allow for enhanced visibility of a tissue site through the manifold area of the third layer 220 between the radial legs 812. The fourth layer 225 of FIG. 8 may also ensure that the dressing 102 continues to provide improved manifolding capability to all portions of the manifold area that may be aligned with a tissue site, including outer edges of the manifold area which may correspond to underlying peri-wound areas of the tissue site.

Figure 9:
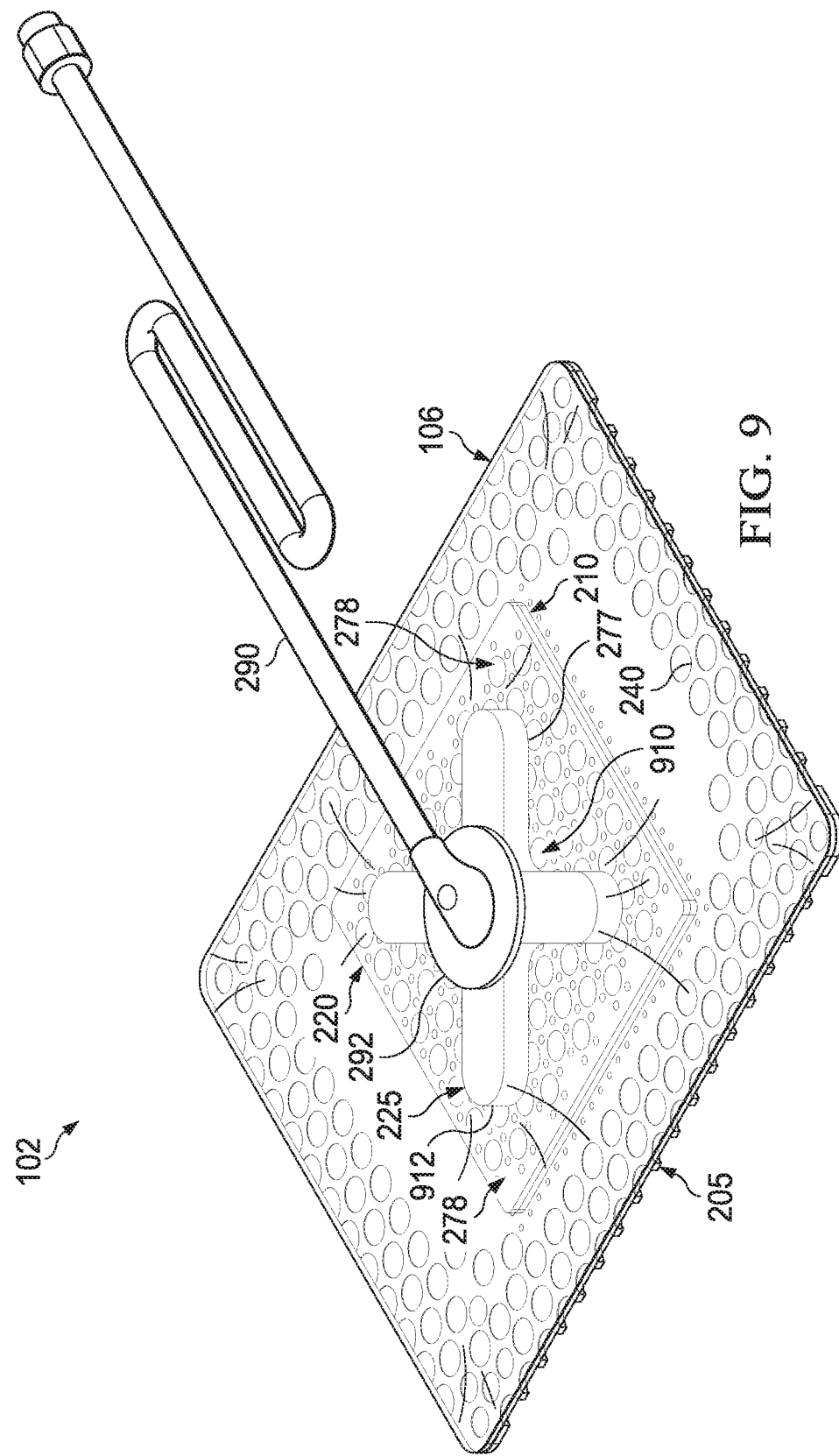
FIG. 9 is a schematic view of another example of a dressing illustrating additional details that may be associated with some example embodiments of the therapy system of FIG. 1.

FIG. 9 is a schematic diagram illustrating a dressing 102 according to additional example embodiments. The tissue interface 108 of the dressing 102 may include a fourth layer 225 in the shape of an 'X' or other similar shape having a central region 910 and appendages, such as radial legs 912, extending from the central region 910. The fourth layer 225 may be placed above or against the manifold area of the third layer 220, and may provide enhanced manifolding to the portions of the manifold area of the third layer 220 placed against the contact area defined by the central region 810 and radial legs 812 of the fourth layer 225. The perimeter of the third layer 220 of the tissue interface 108 may define the borders of a manifold area of the tissue interface 108.

In comparison to the fourth layer 225 of FIG. 8, the fourth layer 225 of FIG. 9 may include larger, but may have fewer appendages, such as radial legs 912, extending from the central region 910. In some embodiments, the radial legs 912 may be shorter in length than the radial legs 812 of FIG. 8, and thus the radial legs 912 may not extend as far toward the outer edges of the manifold area of the third layer 220. However, in some embodiments, the radial legs 912 may each have a greater width than the radial legs 812 of FIG. 8. For example, each of the radial legs 912 may have a width of approximately 25-50% greater than the width of each of the radial legs 812 of FIG. 8. Additionally, the fourth layer 225 of FIG. 9 may have a greater thickness than the fourth layer 225 of FIG. 8. For example, the thickness of the fourth layer 225 of FIG. 9 may be approximately between 4 mm and 10 mm. The fourth layer 225 of FIG. 9 may thus also provide enhanced manifolding to portions of the manifold area of the third layer 220 that are placed against or covered by a portion of the contact area of the 'X'-shaped fourth layer 225. The portions of the third layer 220 that are not covered or placed against a portion of the fourth layer 225, or those portions of the third layer 220 outside of the contact area of the fourth layer 225, may be exposed to the cover 106 of the dressing 102, and thus may remain visible to a user. The configuration of the fourth layer 225 having an 'X' shape may provide for improved visibility through the layers of the tissue interface 108 that correspond to portions of the manifold area of the third layer 220 not associated with the fourth layer 225, which may include a manifold margin 278 around the perimeter of the manifold area as well as some interior portions of the manifold area between the radial legs 912. The fourth layer 225 of FIG. 9 may provide a high level of manifolding to both the inner and outer areas of the manifold area of the third layer 220. The 'X'-shaped fourth layer 225 of FIG. 9 may allow for both good visibility through the manifold margin 278 of the third layer 220 as well as good flexibility of the manifold margin 278 of the third layer 220. The manifold margin 278 may align with the portion of the tissue interface 108 that is for placing or applying against a peri-wound area of a tissue site. Thus, both enhanced visibility through and good flexibility of the tissue interface 108 may be particularly beneficial during application of the dressing 102, when a user may be attempting to align the edges of the manifold area with a portion of the peri-wound area.

Figure 10:
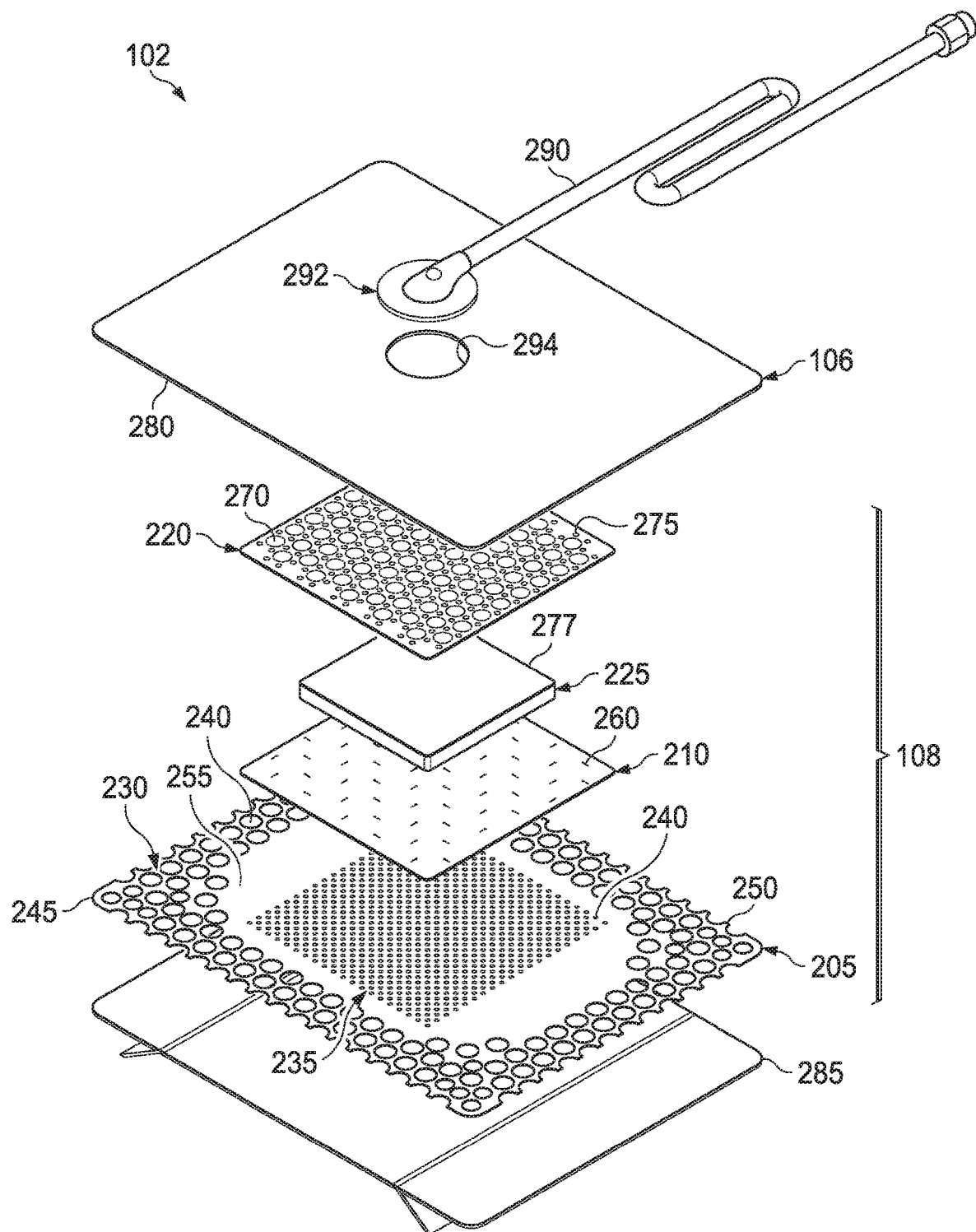
FIG. 10 is an assembly view of another example of a dressing illustrating additional details that may be associated with some example embodiments of the therapy system of FIG. 1.

FIG. 10 is a schematic diagram illustrating another example of the dressing 102. While the components of the dressing 102 of FIG. 10 may be the same as or similar to those of the dressing 102 of FIG. 2, the arrangement and/or order of the layers of the dressing 102 of FIG. 10 may be different. For example, the individual layers of the tissue interface 108 of FIG. 10 may be arranged or stacked in a different order than the layers of the tissue interface 108 of FIG. 2. More specifically, in some embodiments, rather than the fourth layer 225 being placed above the third layer 220, or between the third layer 220 and the cover 106, the fourth layer 225 of FIG. 10 may be placed below or under the third layer 220. Thus, in the example embodiment of FIG. 10, the tissue interface 108 may include a fourth layer 225 positioned between the second layer 210 and the third layer 220. As shown in FIG. 10, the third layer 220 may be oriented so that the blisters 270 are protruding downwards and in contact with the fourth layer 225. In other embodiments, the orientation of the third layer 220 may also be reversed. As shown in FIG. 10, the fourth layer 225 may have a square shape similar to the fourth layer 225 of FIG. 2, however, the fourth layer 225 of FIG. 10 may also have different shapes or configurations, such as the star-shaped configuration or X-shaped configuration of FIG. 8 and FIG. 9, respectively. The fourth layer 225 of FIG. 10 may enhance manifolding through a manifold area of the third layer 220 associated with a contact area defined by a face 277 of the fourth layer 225. The fourth layer 225 may also provide good visibility of the tissue site through the layers of the tissue interface 108 and dressing 102, as the contact area of the fourth layer 225 may be smaller than the manifold area of the third layer 220, the second layer 210, and the first layer 205, all of which may be at least partially transparent.

In some additional or alternative embodiments, the fourth layer 225 may comprise a foam material that allows for an additional degree of visibility through the tissue interface 108. For example, the fourth layer 225 may be formed from a coarse, stiff reticulated foam, such as a 2 pores per inch (ppi) to 3 ppi reticulated foam having a pore size of between about 2 mm to 10 mm. In some embodiments, the foam of the fourth layer 225 may be a Z3SA material, commercially available from FXI of Pennsylvania, USA. Furthermore, the foam of the fourth layer 225 may be made from a non-pigmented polymer, such as a polyurethane, which may provide an additional degree of translucency. In some additional embodiments, the fourth layer 225 may include a portion of coarser foam, such as a 2 ppi to 10 ppi foam, laminated to a portion of perforated 45 ppi foam, such as the foam more typically included in other disclosed embodiments of the fourth layer 225 of the tissue interface 108. In some instances, the fourth layer 225 may have a reduced material content, which may allow for better delivery of possible instilled treatment fluids to an underlying wound and periwound area, as well as develop a higher fluid shear or washing effect of the tissue interfaces.

In some further embodiments, other features may be suitable for the fourth layer 225. For example, rather than a foam material, the fourth layer 225 may be in the form of a non-woven that is perforated with holes having a diameter of between about 5 mm and 10 mm. In further instances, the foam of the fourth layer 225 may be replaced by three-dimensional spacer textiles, where hole formations have been woven into the upper and lower surfaces of the textiles. In some further embodiments, the fourth layer 225 may include a felted perforated foam. In yet further embodiments, the fourth layer 225 may be formed from a foam having large perforations, and the perforations may have various shapes, such as circular, lenticular, polygonal, as well as other shapes. In some cases, larger perforations of the foam may allow the fourth layer 225 to better handle thick or highly-viscous wound exudates.

In yet further embodiments, the fourth layer 225 may be formed from an embossed perforated film, such as a film having bubbles similar to those of the third layer 220, in place of a foam material. The embossed perforated film may provide an improved degree of transparency. In additional embodiments, the fourth layer 225 may comprise one or more layers of a molded mesh or apertured film having a pore size ranging from about 2 mm to 10 mm in diameter, such as materials commercially available from DelStar Technologies, Inc., of Middletown, Del., USA. In some instances, reducing the amount of foam material, or using substitute materials instead of foam for the fourth layer 225, may provide the tissue interface 108 with increased flexibility. The increased flexibility may allow the tissue interface 108 to better conform and seal to traditionally-challenging wound locations, such as joints, feet, hands, amputation sites, and sacral anatomies.

Additional features may also be included in some embodiments of the tissue interface 108. For example, to further aid manifolding in areas of the tissue interface which may be between radial arms of the fourth layer 225, such as the radial legs 812 or radial legs 912 of the embodiments of FIGS. 8 and 9, respectively, portions of the second layer 210 may be embossed. In some instances, the second layer 210 may be embossed on the surface facing away from the tissue site, so as to retain a smooth surface of the second layer 210 that faces the wound or periwound areas of the tissue site. Examples of suitable embossed film for use as the second layer 210 may be available from Charter Nex of Wisconsin, USA. Additionally, some embodiments of the fourth layer 225 may have radial arms formed from reticulated foam, woven or non-woven material, or bubble material with web-like interconnections.

Methods of treating a surface wound to promote healing and tissue granulation may include applying the dressing 102 to a surface wound and sealing the dressing 102 to epidermis adjacent to the surface wound. For example, the first layer 205 may be placed over the surface wound, covering at least a portion of the edge of the surface wound and a periwound adjacent to the surface wound. The cover 106 may also be attached to epidermis around the first layer 205. The dressing 102 may be fluidly coupled to a negative-pressure source, such as the negative-pressure source 104. Negative pressure from the negative-pressure source 104 may be applied to the dressing 102, opening the fluid restrictions 260. The fluid restrictions 260 can be closed by blocking, stopping, or reducing the negative pressure. The third layer 220, the second layer 210, and the first layer 205 can substantially prevent exposure of tissue in the surface wound to the fourth layer 225, inhibiting growth of tissue into the fourth layer 225. The dressing 102 can also substantially prevent maceration of the periwound.

In additional embodiments, methods of treating a surface wound may include applying the dressing 102 to a surface wound and sealing the dressing 102 to epidermis adjacent to the surface wound. The dressing 102 may include a lower layer comprising a first film of at least partially transparent, liquid-impermeable material having a plurality of fluid restrictions to allow the passage of fluid from a wound site through the lower layer. The dressing 102 may further include an upper layer positioned above the lower layer, where the upper layer comprises a second film of a transparent material and further comprising a fluid port for mating with a source of negative pressure. Additionally, the dressing 102 may include an intermediate layer between the lower layer and the upper layer. The intermediate layer may include a foam, and the area of the foam may be less than the area of the lower layer in order to allow visualization of the surface wound underneath the upper and lower layers. The dressing 102 may further include a third film coupled to the lower layer opposite the upper layer, where the third film comprises a hydrophobic material having a plurality of apertures. In some embodiments, the hydrophobic material may be silicone.

The systems, apparatuses, and methods described herein may provide significant advantages over prior dressings. For example, some dressings for negative-pressure therapy can require significant time and skill to be properly sized and applied to achieve a good fit and seal. In contrast, the dressing 102 can be simple to apply, reducing the time to apply and remove. In some embodiments, for example, the dressing 102 may be a fully-integrated negative-pressure therapy dressing that can be applied to a tissue site (including on the periwound) in one step, without being cut to size, while still providing or improving many benefits of other negative-pressure therapy dressings that require sizing. Such benefits may include good manifolding, beneficial granulation, protection of the peripheral tissue from maceration, and a low-trauma and high-seal bond. The dressing 102 may also conform to and occupy a significant space at a tissue site. These characteristics may be particularly advantageous for surface wounds having moderate depth and medium-to-high levels of exudate, and thus may offer significant benefits to tissue sites beyond those including only shallow, surface wounds.

The dressing 102 can also promote granulation while reducing the opportunity for in-growth of granulation tissue into the layers of the tissue interface 108. For example, by containing porous material within other layers comprising materials such as silicone and/or polyethylene, high levels of granulation to the tissue site may be achieved while avoiding significant amounts of tissue in-growth to the dressing 102. Furthermore, macro-strains may be provided to the edges of a tissue site, such as wound edges, while preventing maceration of the surrounding peri-wound area. As a result, reduced trauma to the tissue site upon dressing removal may achieved, while also allowing for longer dressing wear time. Additionally, by including a layer that does not span across the entire manifold area of the other layers of the dressing 102, the dressing 102 may offer the combined benefits of a transparent pressure manifold to offer visibility of the tissue site while also including the superior pressure manifolding capabilities of a foam material optimized for rapid removal of high volumes of fluid. The dressing 102 may promote granulation with reduced possibility of tissue in-growth that can be worn for extended wear times, for example up to seven days. Additionally, caregivers, may be able to visualize the tissue site through portions of the manifold area of the dressing during an extended wear time, without disrupting the dressing.

Another associated advantage of the disclosed dressings may be that the need for a user to size or cut a portion of foam, such as foam associated with the fourth layer 225, to ensure that the foam is positioned in-board of wound edges to avoid irritation and/or maceration to peri-wound tissue, may be eliminated. The need for applying a larger protective border of other layers of a dressing, such as the dressing 102, to the peri-wound area, sometimes known as applying a "window-pane" to the peri-wound area, due to fear of incorrectly sizing the foam granulating layers of the dressing 102, may also be eliminated. For example, the need to apply strips of a protective material around the borders of the tissue site by users who are concerned about a foam or other manifold being in contact with and macerating the peri-wound area, may be reduced or eliminated. Thus, the disclosed dressings may provide a wound filler and/or cover that allows for the management of fluids, manifolds negative pressure, but does not macerate the wound edges or require sizing. Since the opaque foam manifold components of the disclosed dressings may not extend over the entire manifolding area of the other dressing layer(s), users may be able to visualize the wound through the at least partially transparent other layers corresponding to the manifolding area of the dressing, which may make alignment of the manifolding area of the dressing over the wound easier. In some embodiments, the disclosed dressings may also provide compression around the wound, thus reducing oedema. Some embodiments of the dressing 102 may remain on the tissue site for at least 5 days, and some embodiments may remain for at least 7 days. Antimicrobial agents in the dressing 102 may extend the usable life of the dressing 102 by reducing or eliminating infection risks that may be associated with extended use, particularly use with infected or highly exuding wounds. Additionally, some embodiments of the dressing 102 may be used with existing systems for providing negative-pressure and/or fluid instillation therapy to tissue sites.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use. For example, in some configurations the dressing 102, the container 112, or both may be eliminated or separated from other components for manufacture or sale. In other example configurations, the controller 110 may also be manufactured, configured, assembled, or sold independently of other components.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A dressing for treating a tissue site with negative pressure, the dressing comprising:
    a sealing layer including apertures disposed through a periphery and an interior portion of the sealing layer;
    a first film adjacent to the sealing layer and comprising a non-porous material and a plurality of fluid restrictions, wherein one or more of the fluid restrictions is registered with at least one of the apertures in the interior portion, wherein the fluid restrictions extend entirely across the first film;
    a first manifold layer adjacent to the first film and opposite the sealing layer, the first manifold layer comprising a second film of a transparent material having a manifold area comprising blisters and apertures, wherein the apertures in the second film are configured to allow fluid transfer through the second film;
    a second manifold layer adjacent to the first manifold layer, the second manifold layer comprising foam having a contact area that is less than the manifold area; and
    a cover configured to be positioned over the first manifold layer and in contact with at least a portion of the first manifold layer.

2. The dressing of claim 1, wherein at least the first film is configured to be positioned in a stacked relationship between the second manifold layer and the tissue site.

3. The dressing of claim 1, wherein:
    the manifold area has a first shape;
    the contact area has a second shape;
    the first shape is analogous to the second shape; and
    the manifold area comprises a border area around the contact area.

4. The dressing of claim 1, wherein the contact area comprises porous appendages adjacent to the manifold area.

5. The dressing of claim 4, wherein the porous appendages comprise at least three radial appendages adjacent to the manifold area.

6. The dressing of claim 1, wherein the contact area comprises:
    a central region; and
    at least three porous appendages coupled to the central region.

7. The dressing of claim 1, wherein the contact area comprises:
    a central region; and
    at least three porous appendages coupled to the central region and extending to an edge of the manifold area.

8. The dressing of claim 1, wherein the transparent material comprises polyurethane or polyethylene.

9. The dressing of claim 1, wherein the foam is a hydrophobic polymer foam.

10. The dressing of claim 1, wherein the foam is reticulated open-celled foam.

11. The dressing of claim 1, wherein the foam is reticulated polyurethane ether foam.

12. The dressing claim 1, wherein the foam is porous and has an average pore size in a range of 400-600 microns.

13. The dressing of claim 1, wherein the foam has a thickness in a range of 2 millimeters to 7 millimeters.

14. The dressing of claim 1, wherein the blisters are spaced about 2 millimeters apart.

15. The dressing of claim 1, wherein the blisters have a height of about 0.5 millimeters to about 2 millimeters.

16. The dressing of claim 1, wherein the blisters have a width of about 1 millimeter to about 3 millimeters.

17. The dressing of claim 1, wherein the second manifold layer is substantially opaque.

18. The dressing of claim 1, wherein:
the blisters are spaced about 2 millimeters apart;
the blisters have a height of about 1.5 millimeters; and
the blisters have a diameter of about 1.5 millimeters.

19. A method for treating a tissue site, comprising:
positioning a dressing on the tissue site, the dressing comprising:
   a sealing layer including apertures disposed through a periphery and an interior portion of the sealing layer,
   a first film adjacent to the sealing layer and comprising a non-porous material and a plurality of fluid restrictions, wherein the fluid restrictions extend entirely across the first film,
   a first manifold layer adjacent to the first film and opposite the sealing layer, the first manifold layer comprising a second film of a transparent material having a manifold area comprising blisters and apertures, and
   a second manifold layer adjacent to the first manifold layer, the second manifold layer comprising foam having a contact area that is less than the manifold area;
inspecting the position of the dressing against areas of the tissue site by visualizing the areas of the tissue site through at least a border area around the contact area; and
adjusting the position of the dressing so that the manifold area of the dressing substantially corresponds to areas of the tissue site within borders of the tissue site.

20. The method of claim 19, further comprising applying negative pressure to the dressing.

21. The method of claim 19, wherein at least the first film is positioned in a stacked relationship between the second manifold layer and the tissue site.

22. The method of claim 19, wherein the manifold area comprises the border area around the contact area.

23. The method of claim 19, wherein the contact area comprises at least three appendages adjacent to the manifold area.

24. The method of claim 19, wherein the transparent material comprises polyurethane or polyethylene.

25. The method of claim 19, wherein the foam has a thickness in a range of 4 millimeters to 10 millimeters.

26. The method of claim 19, wherein the blisters have a height of about 0.5 millimeters to about 2 millimeters.

27. The dressing of claim 1, wherein the interior portion of the sealing layer corresponds to a surface area of the first film.

28. The dressing of claim 1, wherein the sealing layer is coupled to the cover.

* * * * *